United States Patent
Gough et al.

(10) Patent No.: US 6,759,101 B2
(45) Date of Patent: Jul. 6, 2004

(54) LIQUID CRYSTALLINE MATERIALS CONTAINING PERFLUOROALKYL AND ALKENYL TAIL GROUPS

(75) Inventors: Neil Gough, Longmont, CO (US); Rohini Vohra, Boulder, CO (US); Michael Wand, Boulder, CO (US); Kundalika More, Denver, CO (US); William N. Thurmes, Longmont, CO (US)

(73) Assignee: Displaytech, Inc., Longmont, CO (US)

( * ) Notice: Subject to any disclaimer, the term of this patent is extended or adjusted under 35 U.S.C. 154(b) by 0 days.

(21) Appl. No.: 09/754,034

(22) Filed: Jan. 3, 2001

(65) Prior Publication Data

US 2002/0195585 A1 Dec. 26, 2002

Related U.S. Application Data

(60) Provisional application No. 60/255,984, filed on Dec. 15, 2000.

(51) Int. Cl.$^7$ .................. C09K 19/34; C09K 19/30; C09K 19/12; C09K 19/20; C07D 239/02; C07D 213/00; C07D 25/24; C07C 69/76; C07C 25/13

(52) U.S. Cl. .............. 428/1.1; 252/299.61; 252/299.63; 252/299.64; 252/299.65; 252/299.66; 252/299.67; 252/299.62; 544/303; 544/306; 544/334; 544/335; 546/1; 560/62; 560/65; 570/127; 570/128; 570/130; 570/188

(58) Field of Search .................. 428/1.1; 252/299.61, 252/299.62, 299.63, 299.64, 299.65, 299.66; 544/303, 306, 334, 335, 298; 546/1; 560/62, 65; 570/127, 128, 130, 188

(56) References Cited

FOREIGN PATENT DOCUMENTS

DE    4427199    *    2/1996

OTHER PUBLICATIONS

English abstract of DE–4427199, 1996.*

Inui, S. et al. (1996), "Thresholdless antiferroelectricity in liquid crystals and its application to displays," J. Mater. chem. 6(4):671–673.

Seomun, S.S. et al. (1997), "Evolution of Switchig Characteristics from Tristable to V–Shaped in an apparently Antiferroelectric Liquid Crystal," Jpn. J. Appl. Phys. 36:3586–3590.

* cited by examiner

*Primary Examiner*—Shean C. Wu
(74) *Attorney, Agent, or Firm*—Greenlee, Winner and Sullivan, P.C.

(57) ABSTRACT

Compounds that are useful as components in liquid crystal compositions, particularly in ferroelectric liquid crystal compositions. Compounds of the invention are rod-like molecules with a mesogenic (generally linear) core to which an alkene tail and an alkyl or alkoxy tail with a perfluoroalkyl terminal portion are bonded. Compounds of the invention can contain a variety of one, two or three ring cores, wherein the rings maybe aromatic or alicyclic. Alkenes of the invention are useful as components to improve LC properties of mixtures, for example, to lower melting point of lower freezing point, of LC compositions.

51 Claims, No Drawings

LIQUID CRYSTALLINE MATERIALS CONTAINING PERFLUOROALKYL AND ALKENYL TAIL GROUPS

CROSS-REFERENCE TO RELATED APPLICATIONS

This application takes priority under 119(e) from U.S. provisional application Ser. No. 60/255,984 filed Dec. 15, 2000. This provisional application is incorporated by reference in its entirety herein to the extent that it is not inconsistent with the disclosure herein.

BACKGROUND OF THE INVENTION

The present invention relates to compounds useful as components in liquid crystal (LC) compositions, particularly as components of LC compositions that exhibit smectic phases and more particularly as components of LC compositions that exhibit smectic A and/or smectic C phases. LC compositions of this invention may also exhibit nematic phases. LC compositions of this invention can be ferroelectric liquid crystals (FLCs). The invention also relates to optical devices employing LC compositions of the invention in optical switching and display elements.

Several types of smectic liquid crystal materials (LCs) have been investigated for rapid switching, view-angle enhancement and higher contrast, including surface-stabilized ferroelectric LCs (FLCs), deformed helix ferroelectric LCs (DHFLCs), and antiferroelectric LCs (AFLCs). Recently, smectic material exhibiting thresholdless or more properly V-shaped switching LCs (VSLCs) have been described (Inui, S. et al. (1996) J. Mater. Chem. 6(4): 671–673; Seomun, S. S. et al. (1997) Jpn. J. Appl. Phys. 36:3580–3590). Ferroelectric LCs when aligned parallel to the substrate surfaces using the surface stabilized effect (in an surface-stabilized ferroelectric liquid crystal (SSFLC) device) exhibit two stable state switching on a microsecond time scale. Antiferroelectric LCs exhibit three stable-state switching, which by application of a bias field can be converted for use in a bistable switching mode LC devices. Two of the AFLC states have the same transmittance, so that alternate symmetrical switching can be used in AFLC devices. VLCs, in contrast, exhibit very rapid, analog electro-optic response, allow symmetrical driving, and no dc balance is required. VLCs are particularly attractive for applications requiring generation of multiple levels of gray scale.

Liquid crystal (LC) compositions exhibit one or more LC phases. LC compositions may be composed of one or more components. Components of LC compositions may exhibit liquid crystal phases, have latent liquid crystal phases or be compatible with (not suppress) liquid crystal phases in the LC composition. LC compounds and components of LC mixtures of this invention are rod-like molecules most typically having a generally linear mesogenic core with one or more directly or indirectly linked alicyclic or aromatic rings (which may be fused aromatic rings) and two "floppy tail groups" (i.e., structurally flexible) that may be straight-chain or branched groups positioned on either side of the mesogenic core, e.g.:

The tails often have similar lengths, and both tails are typically longer than four carbons. LC components which do not themselves exhibit liquid crystal phases, but which exhibit LC phases on combination with one or more other components are described as having "latent" liquid crystal phases. Chiral nonracemic LCs useful in FLC, DHFLC, AFLC and VLC compositions have at least one component that has a chiral non-racemic tail group. FLC, DHFLC, AFLC and VLC compositions may be composed entirely of chiral non-racemic components, but are typically composed of a mixture of chiral nonracemic and achiral or racemic components.

SUMMARY OF THE INVENTION

LC compounds of this invention can be chiral nonracemic, chiral racemic or achiral. Compounds of this invention have a substantially linear liquid crystal core and two tails diposed substantially linearly with respect to each other on either side of the core. One tail contains a perfluoroalkyl terminal portion (the portion distal from the core) and the other tail contains a double bond which may be in the cis or trans configuration and which may be positioned internally (i.e., not at the $\alpha$- or $\omega$-positions in the tail) or at the $\alpha$- or $\omega$-positions in the tail with respect to the bond to the core. The perfluoroalkyl tail is achiral and the alkenyl tail can be chiral nonracemic, chiral racemic or achiral.

Compounds of this invention have the formula:

Formula I

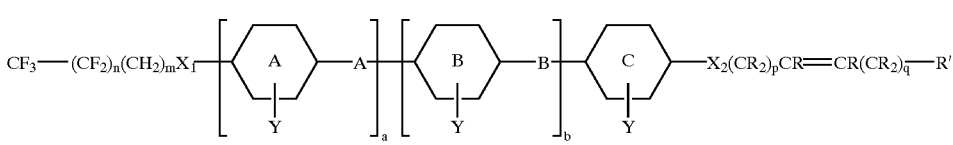

where:

a and b can be 0 or 1, indicating the presence or absence of the group within the brackets; Cores may have one (a=b=0) ring, two rings (a=0) or three rings (a=b=1);

A and B, independently, are linker groups selected from the group consisting of a single bond, —COO—, —OOC—. —CH$_2$—CH$_2$—, —OCH$_2$—, —CH$_2$—O—, —CH=CH— (cis or trans); —C≡C—, —CH=CH—CH=CH— (cis or trans);

Y indicates optional substitution on the core ring and can represent a plurality of substituents which may be the same or different on different ring positions, preferred core ring substituents are fluorine;

Core rings A, B and C can be aromatic or alicyclic and preferably are 6-membered rings, for aromatic rings one or two ring carbon as can be replaced with a heteroatom (a non-carbon atom), particularly N; alicyclic rings can contain 3–10 carbon atoms, preferably contain 5 or 6 carbons and may contain a double bond, one or two CH$_2$ of the alicyclic ring can be replaced with O or a C=O group, more preferred alicyclic rings are cyclohexane and cyclohexene rings; in specific embodiments one, two or three of the A, B and C rings are aromatic; in other embodiments one or two of the A, B or C rings are alicyclic;

m and n are integers ranging from 1 to 20, inclusive; p is an integer ranging from 2 to 20, inclusive; q is 0 or an integer ranging from 1 to 20; inclusive; n+m is 4 to 20 and p+q is 4 to 20;

$X_1$ and $X_2$, independently, are —O— or a single bond; and

R and R', independent of other R or R' in the alkenyl tail are hydrogens, or alkyl groups, particularly lower alkyl groups having from 1 to 6 carbon atoms.

Compounds of this invention include compounds of the above formula having any one of the cores listed in Scheme 1.

In a specific embodiment, compounds of this invention have the formula:

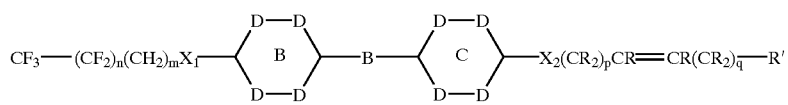

Formula II where n, m, p, q, n+m, p+q, $X_1$, $X_2$, B, Ring B and Ring C can take values as noted above and each D, independent of other D's, can be CH or $CH_2$, a nitrogen atom, CY or CHY, where Y is a CN, $NO_2$, an alkyl, a perhaloalkyl (e.g., perfluoralkyl), or a halide, particularly a fluorine. Rings B and C can be alicyclic or aromatic and B and C that are aromatic can be fused ring systems, such as naphthalene. One of B or C can also be a fused ring system that is partially aromatic, such as a dehydronapthalene ring system. In particular embodiments, both of rings B and C are aromatic, or one of B and C is aromatic and the other of B or C is alicyclic, particularly a cyclohexane or cyclohexene ring. In preferred embodiments: (1) all D's are CH; (2) one or two D's are N and the remaining D's are CH; (3) one or two D's are CF and the remaining D's are CH; (4) one or two D's are N, one or two D's are CF and the remaining D's are CH; (3) all D's on one ring are $CH_2$ and one, two or three D's on the other ring can be N or CF; (4) all D's on one ring are $CH_2$ and all D's on the other ring are CH.

In a further specific embodiment, compounds of this invention have the formula:

where each D independent of other D's can be CH or CY as defined above or a nitrogen atom and all other variables are as defined above. In preferred compounds of Formula III, all D's are CH or one or two D's can be CF or nitrogen with the remaining D's being CH. In preferred embodiments, the core is a phenylpyrimidine, a phenylpyridine, phenylbenzoate, or biphenyl.

In another specific embodiment, compounds of this invention can have the formula:

Formula IV

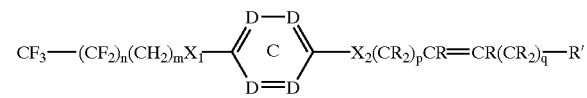

where each D, independent of other D's, can be CH, CY or a nitrogen. In preferred compounds of Formula IV, all D's are CH or one or two D's can be CF or nitrogen with the remaining D's being CH.

In yet another specific embodiment, compounds of this invention can have the formula:

Formula V

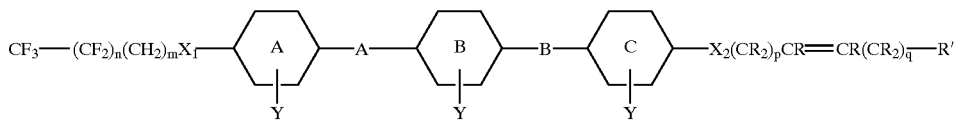

where variable have the values listed in Formula I above. In particular embodiments the core can be (1) an optionally substituted terphenyl, where the preferred substitution is one or two F's; (2) a core in which A or C is a cyclohexane or cyclohexene ring and the remaining rings are aromatic; (3) a core in which A or C is a cyclohexane or cyclohexene and the remaining rings are selected from phenyl rings, phenyl rings substituted with one or two F's, pyrimidine rings or pyridine rings; (4) a core in which A or C is a cyclohexane or cyclohexene and the remaining tow rings represent a phenylpyrimidine, a phenylpyridine, a phenyl benzoate or a biphenyl.

Compounds of this invention include those of the above Formulas I–V which exhibit a smectic C phase that extends Formula III

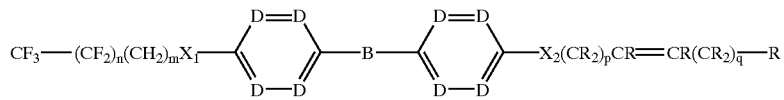

over a temperature range of at least 30° C., as well as those which exhibit a smectic C phase that extends over a temperature range of at least 50° C. Compounds of this invention include those of the above formula which exhibit both a smectic C phase and a smectic A phase. The presence of a smectic A phase in combination with a smectic C phase in an FLC composition facilitates alignment of the composition in an LC cell resulting in fewer layer defects and higher contrast devices. The presence of a nematic phase in addition to a smectic A and smectic C phase further facilitates alignment of the composition in an LC cell resulting in fewer layer defects and higher contrast devices. Compounds of this invention include those of the above formulas that do not themselves exhibit any liquid crystal phase, but which in combination with one or more LC compounds, including one or more LC compounds of this invention, exhibit liquid crystal phases, particularly smectic LC phases.

The invention provides LC compositions comprising one or more of the compounds of this invention as described above. LC compositions of the invention include those that contain sufficient amounts of one or more of the compounds of this invention to have a substantial effect upon the physical or optical properties of the LC composition in which they are combined or to which they are added. A substantial effect upon the physical or optical properties of the LC compositions includes, among others, a significant change in a LC property of the composition, birefringence, switching speed, alignment or contrast. LC compositions of this invention include those that contain from about 1% to 100% by weight of one or more compounds of this invention. LC compositions of this invention include those that contain 3% or more of one or more of the compounds of this invention. LC compositions of this invention include those that contain 3% or more of one or more of the compounds of this invention LC compositions of this invention include those that contain 5% or more of one or more of the compounds of this invention. LC compositions of this invention include those that contain 10% or more of one or more of the compounds of this invention. LC compositions of this invention include those that contain 20% or more of one or more of the compounds of this invention. LC compositions of this invention include those that contain 50% or more by weight of one or more of the compounds of this invention.

LC compositions of this invention include those that are ferroelectric liquid crystal compositions, particularly those that exhibit smectic phases, and more particularly those that exhibit a smectic A phase and/or a smectic C phase. LC compositions of this invention include those that comprise one or more of the compounds of this invention and which exhibit a smectic C phase that has a temperature range of 30° C. or more. LC compositions of this invention include those that comprise one or more compounds of this invention and which exhibit a smectic C phase that has a temperature range of 50° C. or more. In preferred compositions, the temperature range of the smectic C phase includes room temperature (about 20° C.). LC compositions of this invention include those comprising one or more compounds of this invention and which are chiral nonracemic. LC compositions of this invention include those comprising one or more compounds of this invention and which are chiral racemic or achiral. LC compositions of this invention also include those that consist essentially of two or more of the compounds of this invention and those in which the composition consists of a mixture of at least two of the compounds of this invention.

The invention includes FLC host mixtures that comprise one or more achiral or chiral racemic compounds of this invention, FLC host mixtures that consist essentially of one or more achiral or chiral racemic compounds of this invention and FLC host mixtures that consist of at least two achiral or chiral racemic compounds of this invention.

Addition of one or more compounds of this invention to mixtures of LC's can result in changes in physical or optical properties of those mixtures that make the resulting mixtures improved for applications in optical devices. In particular, the addition of one or more of the compounds of this invention can broaden the smectic C range of a given mixture. The addition of one or more of the compounds of this invention can improve alignment of a given LC or FLC mixture in a cell, leading to improved contrast in the optical device employing the LC or FLC cell. Of particular benefit, the compounds of this invention are compatible with (i.e., do not significantly detrimentally affect the properties of) LC and FLC materials that exhibit true bookshelf alignment. LC compounds exhibiting true bookshelf alignment are described for example in pending U.S. applications No. 60/229,892, filed Sep. 1, 2000 and Ser. No. 09/653,437 filed Sep. 1, 2000, which are incorporated by reference herein to provide examples of LC compounds which may be combined with the compounds of this invention to provide useful LC and FLC compositions. U.S. provisional application No. 60/256,063 filed Dec. 15, 2000, and No. 60/256,229, filed Dec. 15, 2000 also provide examples of LC compounds that may be combined with the compounds of the present invention to provide useful LC and FLC compositions. U.S. regular application No. 09/754,033 filed Jan. 3, 2001, and Ser. No. 09/753,749 filed Jan. 3, 2001 (commonly owned and concurrently filed with this application) and which take priority from the provisional applications filed Dec. 15, 2000 also provide examples of LC compounds that may be combined with the compounds of the present invention to provide useful LC and FLC compositions.

LC and FLC compositions of this invention are useful in the preparation of optical devices, particularly for optical switching devices and displays. Those of ordinary skill in the art understand how to make LC and FLC cells and devices that utilize the compositions of this invention. In particular, methods and techniques are known and available in the art for alignment of LC and FLC compositions between substrate layers to form optical elements that exhibit true bistable, near bistable, or tristable state switching or optical elements that exhibit analog behavior. Various methods and techniques for constructing LC and FLC cells and for use of such cells are known in the art and can be readily adapted for use with compositions of this invention. The compositions of this invention are particularly well suited for providing devices that can operate (in a smectic C phase, for example) over a broad temperature range.

DETAILED DESCRIPTION OF THE INVENTION

The invention relates generally to compounds that are useful as components in LC compositions. LC compositions typically contain a plurality of components, some of which exhibit LC phases, which when combined exhibit LC phases. LC compositions of most interest are those which exhibit a desired LC phase over a temperature range that facilitates practical application of the composition in an optical device. For example, LC materials exhibiting a smectic C range around normal room temperature can be employed in device applications. Preferred LC materials will exhibit the desired LC phase over a broad, useful temperature range which facilitates device stability. Preferred LC materials will exhibit a desired LC phase with temperature range that minimizes or avoids crystallization of components of the LC composition during operation or storage of an optical device. Compounds of this invention can improve (broaden or shift) the temperature range of desired LC phases in LC compositions to which they are added. In particular, compounds of this invention can be employed to broaden or shift the temperature range of smectic C phases of LC compositions. The compounds may also be added to lower the temperature at which crystallization of an LC composition occurs to improve storage lifetime of an LC device containing the LC composition. Benefit is assessed as lowering of the melting point of the compositions and/or as lowering of the freezing point of the mixture. A significant improvement in LC stability can be obtained with even a 2° C. lowering of melting point, if that lowering is obtained without a significant negative effect on other LC properties. LC compositions of this invention include those in which the melting point of the LC composition is decreased by at least 4 or 5° C. by addition of one or more compounds of this invention without significant detrimental effect on other LC phase properties. In some compositions addition of 10 weight % of less of one or more compounds of this invention can achieve a lowering of 4 or 5° C. Significant improvements in LC stability can be achieved by lowering the freezing point of a mixture. LC compositions of this invention include those in which the freezing point of the LC composition is decreased by at least 5° C. or by at least 10° C. without significant detrimental effect on other LC phase properties by addition of one or more compounds of this invention. Again in some compositions, an addition of 10 weight % of one or more compounds of this invention can achieve a lowering of the freezing point by 5° C. or 10° C. LC compositions comprising one or more of the compounds of this invention and exhibiting a freezing point of −60° C. or lower are of particular interest. Those compositions which exhibit a FP of −60° C. or lower and contain 10% by weight or less of a compound of this invention are particularly useful. LC compositions often exhibit a freezing point significantly lower than the melting point, indicative of supercooling. Preferred LC mixtures of this invention exhibit a freezing point that is significantly lower than the melting point of this invention. LC compositions of this invention include those in which the difference in the melting point and freezing point, i.e., |MP−FP| (absolute value of the difference of the MP and FP) of the composition is increased by 10° C. without significant detrimental effect on other LC phase properties by addition or one or more compounds of this invention. In some cases, an addition of 10 weight % of one or more compounds of this invention can result in a significant differential lowering, approaching 10° C., of FP compared to MP of a mixture.

Compounds of this invention can impart additional beneficial optical or physical properties to LC compositions to which they are added. Properties that can be affected include: viscosity (decreased viscosity results in faster optical switching), tilt angle, birefringence, LC layer structure (the ability of the LC to form a desired layer structure, e.g., to form a true bookshelf structure), and alignment of layers between substrates (the ability of the LC to be aligned with minimal defects which are detrimental to device contrast). Preferred LC compositions of this invention include those in which addition of one or more compounds of this invention (Formulas I–V) results in a significant improvement of 10% or more in a physical or optical property of the mixture to which they are added.

Compounds of Formulas I–V are useful in the preparation of LC and FLC compositions which in turn are useful in various optical device applications.

Subsets of compounds of Formula I–V that are useful in the preparation of LC and FLC compositions include those in which:

the core is a phenylbenzoate, a biphenyl, a terphenyl, a phenyl pyrimidine, a phenylpyridine, a tolane or a biphenyl-phenyl, any of which may be substituted with one or two fluorines;

the core contains two aromatic rings;

the core contains three aromatic rings;

the core contains two aromatic rings and one alicyclic ring;

the core contains one cyclohexane rings and one optionally substituted phenyl ring;

the core contains two cyclohexane rings and one optionally substituted phenyl ring;

the core contains one cyclohexene ring to which the alkene tail is attached;

both of $X_1$ and $X_2$ are oxygen atoms;

one of $X_1$ or $X_2$ is an oxygen and the other is a single bond;

$X_1$ is oxygen and $X_2$ is a single bond;

one or two of D in the core are CF;

n+m is 5–12;

n+m is 7–10;

n and m are 3, 4, 5 or 6;

q is zero;

q is zero and p is 5 to 12, inclusive;

p and q are 3, 4, 5 or 6;

p+q is 5 to 12;

p+q is 7–10;

p=q or n=m;

both p=q and n=m;

the double bond in the alkenyl tail is a cis double bond;

the double bond in the alkenyl tail is a trans double bond;

R' is an alkyl group having from 1 to 6 carbon atoms, inclusive;

R' is a methyl group;

all of R and R' are hydrogens;

all of R are hydrogens;

one or two of R are alkyl groups having from 1 to 6 carbon atoms, inclusive;

one R positioned within 3–5 carbons of the bond to the core is an alkyl group having from 1 to 6 carbon atoms, inclusive;

one R positioned at the $5^{th}$ carbon or more from the bond to the core is an alkyl group having from 1 to 6 carbon atoms, inclusive;

one R positioned within 1–3 carbon atoms of the bond to the core is an alkyl group having from 1 to 6 carbon atoms;

the core has one of the structures:

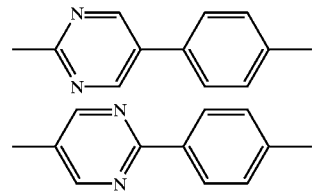

-continued

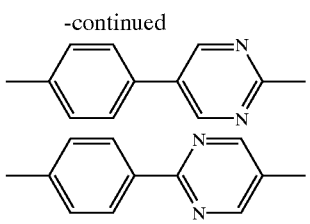

Compounds of this invention particularly useful in the preparation of include those in which:

the core is a phenyl pyrimidine (which may be substituted with one or two fluorines), $X_1$ is oxygen, $X_2$ is a single bond, and (1) all of R and R' are hydrogens;
(2) one, two or three of R or R' are alkyl groups having from 1 to 6 carbon atoms, inclusive;
(3) q is zero and R' is hydrogen;
(4) n and m are 3–7;
(5) n and m are 4, 5 or 6;
(6) n+m is 8, 9 or 10;
(7) p and q are 3–7;
(8) p and q are 4, 5, or 6;
(9) p+q is 8, 9, or 10;
(10) the double bond in the alkenyl tail is a cis double bond;
(11) the double bond in the alkenyl tail is a trans double bond;
(12) one R or R' positioned within 5 carbons of the core is a methyl group and ethyl group or a propel group;
(13) one R or R' positioned on a carbon at least 5 carbons from the core is a methyl, ethyl or propel group;
(14) n and m are both 4;
(15) n and m are both 4 and p+q is 8–10;
(16) n and m are both 4; p+q is 8 to 10; R and R' are all hydrogens;
(17) n and m are both 4; p+q is 8 to 10; R and R' are all hydrogens; and the double bond is in the trans configuration;
(18) n and m are both 4; p+q is 8 to 10; R and R' are all hydrogens; and the double bond is in the cis configuration;
(19) n and m are both 4; p+q is 8 to 10; R and R' are all hydrogens; and q is zero; and
(20) p=q and all R and R' are hydrogens.

Compounds of the invention useful in the preparation of LC compositions also include those in which:

the core is phenyl pyrimidine; and one or both of $X_1$ and $X_2$ are oxygen atoms and optionally other variables have the values listed in 1–20 above;

the core is phenylpyridine; $X_1$ is an oxygen atom and $X_2$ is a single bond and optionally other variables have the values listed in 1–20 above;

the core is phenylpyridine; $X_1$ and $X_2$ are both oxygen atoms and optionally other variables have the values listed in 1–20 above;

one or two of the D moieties of the core are a nitrogen atom and one or two are CF; $X_1$ is an oxygen atom and $X_2$ is a single bond and optionally other variables have the values listed in 1–20 above;

the core is a phenyl pyrimidine; $X_1$ and $X_2$ are oxygen atoms; all R and R' are hydrogens; p+q is 8–10 (inclusive) and n+m are 8–10 (inclusive); and optionally other variables have the values listed in 1–20 above;

the core is a phenyl pyrimidine; $X_1$ and $X_2$ are oxygen atoms; all R and R' are hydrogens; and the double bond is cis; and optionally other variables have the values listed in 1–20 above;

the core is a phenyl pyrimidine; $X_1$ and $X_2$ are oxygen atoms; all R and R' are hydrogens; and the double bond is trans; and optionally other variables have the values listed in 1–20 above; or the core is phenyl pyrimidine; $X_1$ and $X_2$ are oxygen atoms; n=m=4; and optionally other variables have values as listed in 1–20 above.

Exemplary cores of compounds of this invention are listed in Scheme 1. The alkene tail can be on either side of the cores of Scheme 1.

Compounds of this invention can have a core with a single aromatic ring, e.g., a phenyl ring, a pyridine ring, or a pyrimidine ring, each of which can be optionally substituted with one to four substituents, particularly halides, CN, $NO_2$, alkyl, alkoxy and more particularly F.

Compounds of this invention also include chiral nonracemic compounds of formulas I–V in which the alkene tail is a chiral nonracemic moiety. For example, the alkene tail can be a chiral nonracemic tail of formula I in which one R bonded to the third to the fifth carbon in the tail is a methyl group and the carbon to which the methyl group is bonded is an asymmetric carbon. The alkene tail of this invention can have the formula:

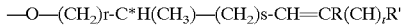

where r is an integer ranging from 1 to 4, s is an integer ranging from 1 to 6, t is an integer ranging from 0 to 6, R and R', independently, are H or a lower alkyl group (1–6 carbon atoms), particularly a methyl group. Alkene tails also include those of the formula above in which r is 2, 3 or 4, s is 2 to 6 and t is 0. Specifically the alkene tail can have the formula: $-O-(CH_2)_r-C^*H(CH_3)-(CH_2)_s-CH=C(CH_3)_2$ where r is 2–4, inclusive, and s is 2–6, inclusive.

As used herein the term alkyl refers generally to straight-chain and branched alkyl groups. Alkyl groups can include lower alkyl groups (those having from 1–6 carbon atoms) and higher alkyl groups (those having about 7 or more carbon atoms), unless otherwise noted. The term alkoxy group refers to groups having a terminal oxygen atom (—O-alkyl). For example, alkoxy tail groups are attached to the core via the terminal oxygen. The alkyl portion of an alkoxy group includes straight-chain and branched alkyl groups and unless otherwise noted includes lower alkyl and higher alkyl groups. Alkyl groups, including those of alkoxy group, typically have less than 20 carbons and preferably, dependent upon the specific structure, have 12 or fewer carbon atoms. In compounds where alkyl or alkoxy tail groups are specified, preferred alkyl groups have from 5 to 12 carbon atoms and more preferred alkyl groups have 6 to 10 carbon atoms.

As used herein the term alkene refers generally to any group containing one or more double bonds. The alkene tails of this invention as specified in Formulas I–V contain a single double bond. Alkene tails include alkanes tails, i.e., —O-alkene, in which the alkene group has a terminal oxygen atom which forms the bond to the core. In general the double bond of the alkene tail can be positioned anywhere in the chain, but preferably is located 2 or more carbons from the end of the tail attached to the core. The alkene may contain an omega double bond, but the double bond is more preferably located away from the ends of the tail. The double bond may be in the cis or trans configuration.

The term alicyclic generally refers to alkyl or alkene groups that contain a cyclic portion. An alicyclic group can be a saturated ring or unsaturated ring, such as a cyclohexane or cyclohexene ring. Alicyclic rings can contain one or more (typically one) heteroatoms, e.g., O, N or S, in place of ring $CH_2$ groups. Further, one or more (typically one) ring $CH_2$ groups can be replaced with C=O groups. Alicyclic groups of the cores of this invention are optionally substituted (unless otherwise noted). Preferred substituents include lower alkyl groups, lower alkene groups, halogens, CN and $NO_2$ groups. Preferred halogen substituents are fluorines. In general, all, but two aromatic ring positions (e.g., the positions for linkages to tails or to other core rings) can carry non-hydrogen substitutents. However, more typically one or two ring positions (in addition to the linkages to the tails or other cores) can be substituted.

The term aromatic generally refers to a group containing at least one aromatic ring, e.g., a phenyl ring. Aromatic rings typically are have five or six-member aromatic rings. Aromatic rings can also include fused aromatic rings, such as naphthalene or dehydronapthalene rings (see Scheme 1). An aromatic ring can contain one or more (typically one or two) heteroatoms, e.g., O, N or S. Aromatic groups of the cores of this invention are optionally substituted (unless otherwise noted). Preferred substituents include lower alkyl groups, lower alkene groups, halogens, CN and $NO_2$ groups. Preferred halogen substituents are fluorines. In general, all, but two positions on the ring can be substituted (e.g., the positions for linkages to tails or to other core rings). However, typically one to four positions of the ring can be substituted and more typically one or two ring positions (in addition to the linkages to the tails or other cores) can be substituted. Preferred substituted aromatic rings have one position substituted with a lower alkyl or alkene group, a CN group or a $NO_2$ group. Additionally preferred substituted aromatic rings have one or two positions substituted with one or two halogens, and the preferred halogen is fluorine.

Specific examples of compounds of this invention are illustrated in Scheme 2.

Exemplary methods for synthesis of the compounds of this invention are provided in the Examples 1–5. Compounds of this invention can be readily synthesized in view of the guidance provided herein and by application of methods that are well-known in the art.

Exemplary LC mixtures comprising one or more compounds of this invention are listed in Table 1 which provides phase diagrams, and various properties of the listed mixtures. The compositions of the mixtures of Table 1 are provided in Tables 3–15 and the structures of specific components of the mixtures of Tables 3–15 are provided in Scheme 3. Table 2 provides properties of several additional mixtures. Properties of polarization, viscosity, electric rise time, resistivity, dielectric constant of the mixtures are given in Tables 1 and 2 as well as the melting point (MP) and freezing point (FP) as measured by differential scanning calorimetry. The lower temperature limit on the instrument used to provide FP measurements is −60° C., so table entries of FP of −60° C. indicate that the FP was less than or equal to −60° C. The properties listed in these tables are measured using techniques that are well-known in the art. In the tables, I means isotropic, N means nematic, A means smectic A, C means smectic C, SI means smectic I and Sx (or S?) means unidentified smectic phase.

Chiral nonracemic LC mixtures for which data is provided in Table 1 include those comprising one or two compounds of this invention in amounts ranging from about 4% by weight to about 20% by weight of the mixtures. Table 2 compares two mixtures MX 9295 (containing compound 1598 of this invention, see Table 3) with MX 9244 (a mixture that does not contain a alkene of this invention, see Table 15 and Scheme 3). Tables 16 provides the results of additional comparisons of properties of mixtures with and without addition of an alkene of this invention. MX 9480 is a mixture containing 10 weight % of MDW 1598 (Scheme 2) in base mixture 8818 (Composition given in Table 17). MX 9486 is a mixture of 10 weight % MDW 1028 (Scheme 2) in base mixture 8818. MX 9480 exhibits a significant lowering of freezing point along with a decrease in MP compared to the base mixture (containing no alkene of this invention). Further, MX 9486 exhibits a 3–4° C. increase in the transition temperature from the smectic C to the smectic A phase. Note that the other LC properties of the mixture are not significantly effected by the addition of MDX 1598. Optical and switching properties of MX 9480 have not been optimized. MX 9486 exhibits a significant lowering of freezing point along with a decrease in MP compared to the base mixture (containing no alkene of this invention). Further, MX 9480 exhibits about a 3° C. increase in the transition temperature from the smectic C to the smectic A phase. Note that the other LC properties of the mixture are not significantly effected by the addition of MDX 1598. Optical and switching properties of MX 9486 have not been optimized.

Schemes 3 and 4 provide exemplary components that can be combined with one or more of the compounds of this invention to obtain useful LC and FLC compositions. Scheme 3 provides specific compounds the use of which is exemplified in the compositions of Tables 3–15 and 17. Scheme 4 provided compounds of structures 1–20 illustrating components, including achiral or chiral racemic components, which can be combined with one or more of the compounds of this invention to obtain a LC mixture, particularly mixtures that exhibit smectic phases, and more particularly mixtures that exhibit smectic C phases and optionally smectic A phases. In such mixtures one or more of the alkenes of this invention is combined with one or more of the compounds of structures 1–20. LC mixtures of this invention include those which combine one or more alkenes of this invention with one or more phenylpyrimidines of structure 9, and in particular include those which contain a total of about 2 to about 25 weight % of one or more compounds of this invention and a total of about 10–80 weight % of one or more compound of structure 9. LC mixtures of this invention also include those which combine one or more alkenes of this invention with one or more compounds of structures 11 and 12, and in particular include those which contain a total of about 2 to about 25 weight % of one or more compounds of this invention and a total of about 10 to about 40 weight % of one or more compounds of structures 11 and 12. LC mixtures of this invention also include those which combine one or more alkenes of this invention with one or more compounds of structure 10 and in particular include those which contain a total of about 2 to about 25 weight % of one or more compounds of this invention and a total of about 5 to about 50 weight % of one or more compounds of structure 10. Of particular interest are mixtures which contain at least three terphenyl compounds of structure 10, each of which is substituted with two fluorines on a different ring of the core. The use of such terphenyl compounds in LC compositions is described in U.S. Pat. No. 5,278,680, which is incorporated by reference herein. LC mixtures of this invention can further contain one or more compounds of structure 13, and in particular can contain from about 5 to about 15 weight % of one or more compounds of structure 13. LC mixtures of this invention can combine components of structure 9, components of structures 11 or 12, components of structure 10 and optionally components of structure 13 with one or more alkenes of this invention. Compounds of structures 14–16 are optional, but preferred components of LC compositions of this invention, particularly when the cyclohexene ring of the core carries an alkene tail.

Structures 17–20 (in Scheme 4) illustrate exemplary chiral non-racemic components that can be employed to prepare chiral nonracemic LC mixtures, particularly those chiral nonracemic LC mixtures that exhibit smectic phases. These chiral nonracemic compounds include those having a partially fluorinated tail. Chiral nonracemic compounds having an achiral tail that is partially fluorinated, i.e., having a terminal perfluorinated portion (e.g., —O—(CH$_2$)$_4$—C$_4$F$_9$), exhibit enhanced polarization in host mixtures and provide high polarization mixtures with improved switching speed. Chiral nonracemic enantiomers of the compounds of structures 17–20 can also be employed in the mixtures of this invention. LC compositions of this invention include those which contain one or more of the alkene compounds of this invention in combination with up to a total of about 25% by weight of one or more of compounds 17–20 of Scheme 4. LC compositions further include those which combine one or more compounds of structure 9, one or more compounds of structure 10, or one or more compounds of structures 11 or 12 with one or more alkene compounds of this invention and one or more of the chiral nonracemic compounds of structures 14–17. Chiral nonracemic compounds of this invention can also include one or more compounds of structure 13.

Compounds of structures 1–20 can be prepared by methods that are well known in the art from readily available starting materials. Methods that are useful in the preparation of various LC compounds and FLC compounds are provided, for example, in U.S. Pat. Nos. 5,051,506; 5,061,814; 5,130,048; 5,167,855; 5,178,791; 5,178,793; 5,180,520; 5,271,864; 5,278,680; 5,380,460; 5,422,037; 5,453,218; 5,457,235; 5,539,555; 5,543,078; 5,585,036; 5,626,792; 5,637,256; 5,658,493; 5,753,139; 5,866,036; and 6,139,771. Each of which is incorporated by reference herein for synthetic methods applicable to the synthesis of compounds of this invention including compounds of structures 1–20. High polarization dopants of structures 18 and 20 are described in concurrently filed U.S. provisional application Attorney Docket No. 75-99, which is incorporated by reference herein. The listed patents along with U.S. Pat. Nos. 5,168,381 and 5,596,434 also provide detail of how LC and FLC compositions of this invention can be applied for the production of LC cells and optical devices.

The following examples further illustrate the invention, but are not intended to limit the invention.

EXAMPLE 1

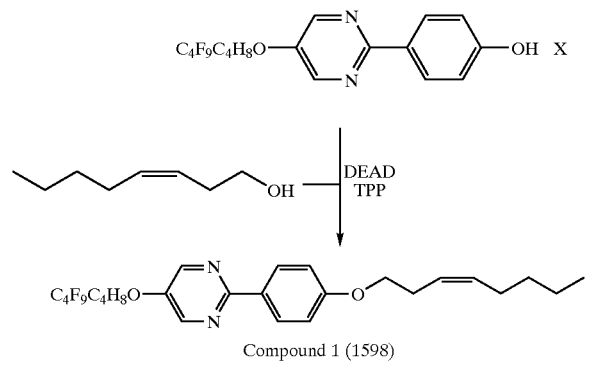

Compound 1 (1598)

1. Cis-5-(5,5,6,6,7,7,8,8,8-Nonafluoro-octyloxy)-2-(4-oct-3-enyloxy-phenyl)-pyrimidine A solution of DEAD (0.261 g, 1.50 mmol) in THF (20 ml) was added dropwise to a stirred solution of 4-[5-(5,5,6,6,7,7,8,8,8-nonafluorooctyloxy)-pyrimidin-2-yl]-phenol (0.858 g, 1.50 mmol), cis-3-octene-1-ol (0.192 g, 1.50 mmol) and triphenylphosphine (0.939 g, 1.50 mmol) in THF (30 ml) and the reaction mixture stirred at room temperature for 24 h. The solvent was removed in vacuo and the residues purified by column chromatography [silica gel, eluted with hexane/ethyl acetate (4:1)] to yield a colorless solid, which was recrystallized from ethanol.

Yield: 00.43 g, 0.63 mmol, 42%

Transitions: Cr 59.0 SmC 109.6 I 109.6 SmC 46.4 Cr ° C.

Synthesis of X

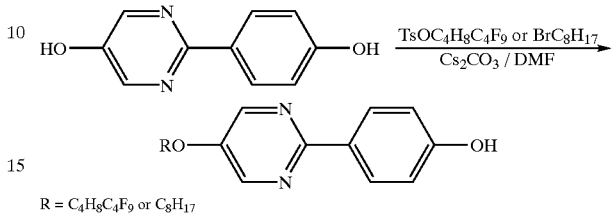

R = C$_4$H$_8$C$_4$F$_9$ or C$_8$H$_{17}$ 4-(2-(5-alkoxypyrimidyl))phenol 25 mmol of alkyltosylate or bromide, 25 mmol of pyrimidylphenol derivative, 30 mmol of Cs$_2$CO$_3$ and 50 ml of DMF were mixed together and stirred at RT over night. The reaction mixture was then poured into water. The solid was filtered and washed with water. The crude product was dissolved in ethyl acetate, washed with water and dried over MgSO$_4$. After evaporation of solvent, the residue was purified by flash chromatography. The yield is 65%.

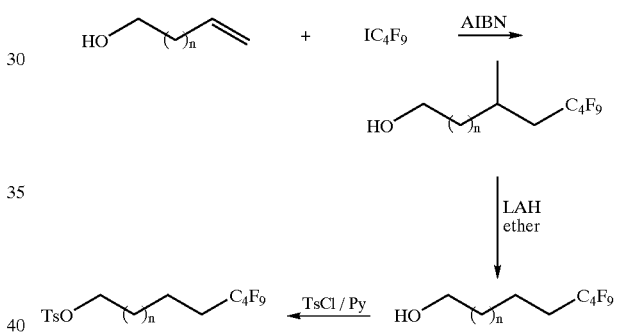

7,7,8,8,9,9,10,10,10-Nonafluoro-5-iodo-decanol

To the mixture of 5 g of 5-hexenol and 17.4 g of perfluoro iodobutane, was added 110 mg of AIBN at RT under N$_2$ atmosphere. After 15 mins, another 110 mg of AIBN was added. The resulting solution was then refluxed at 70° C. for 4 hrs. The reaction mixture was cooled down and used for the next reaction without further purification.

7,7,8,8,9,9,10,10,10-Nonafluoro-decanol

To the solution of 2 g of LAH in 120 ml of abs. ether, was added slowly ca. 22 g of 7,7,8,8,9,9,10,10,10-Nonafluoro-5-iodo-decanol derivative in 30 ml abs. Ether. After addition, the reaction mixture was stirred at RT for two days and then cooled down to 5° C. in the ice water. Water was added slowly until no gas evolved. The solid was filtered through short column of silica gel, washed with ether and ethyl acetate. The filtrate was combined and the solvent was evaporated. The residue was distilled under vacuum to give 13 g (81% yield) of the partial-fluoro alcohol.

7,7,8,8,9,9,10,10,10-Nonafluoro-decyl tosylate

The solution of 9.8 g of partial-fluoro alcohol in 40 ml of pyridine was cooled down to 0° C. in ice-salt water and 6 g of TsCl was added in small portion. After addition the resulting mixture was stirred at 0° C. for two hours and then placed in freezer (−20° C.) for two days. The reaction mixture was poured into ice water and the product was extracted with ethyl acetate twice. The combined organic phase was washed with brine, 10% HCl and again brine three times, and then dried over $MgSO_4$. After evaporation of solvent, pure partial-fluoro tosylate was obtained in yield of 98%.

EXAMPLE 2

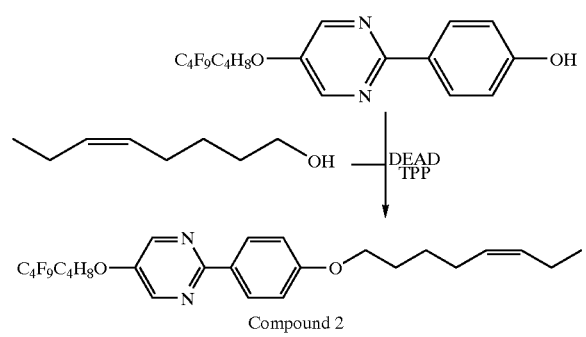

Compound 2

2. Cis-5-(5,5,6,6,7,7,8,8,8-Nonafluoro-octyloxy)-2-(4-oct-5-enyloxy-phenyl)-pyrimidine A solution of DEAD (0.261 g, 1.50 mmol) in THF (20 ml) was added dropwise to a stirred solution of 4-[5-(5,5,6,6,7,7,8,8,8-nonafluorooctyloxy)-pyrimidin-2-yl]-phenol (0.858 g, 1.50 mmol), cis-5-octene-1-ol (0.192 g, 1.50 mmol) and triphenylphosphine (0.939 g, 1.50 mmol) in THF (30 ml) and the reaction mixture stirred at room temperature for 24 h. The solvent was removed in vacuo and the residues purified by column chromatography [silica gel, eluted with hexane/ethyl acetate (4:1)] to yield a colorless solid, which was recrystallized from ethanol.

Yield: 0.35 g, 0.51 mmol, 34%

Transitions: I 114.6 SmA 113.8 SmC 61.7 Cr, Cr70.7 SmC 113.8 SmA 115.4 I ° C.

EXAMPLE 3

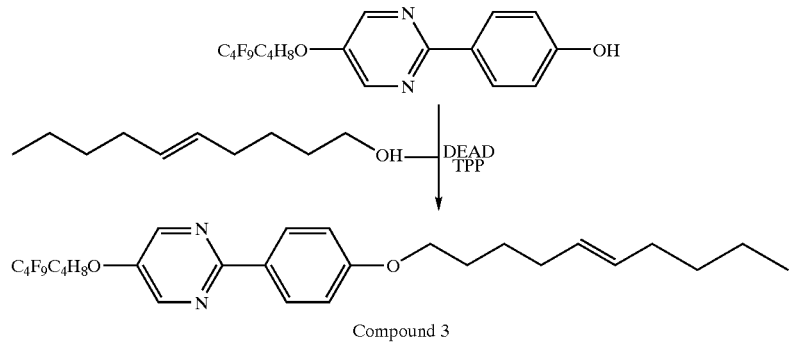

Compound 3

3. Trans-2-(4-Dec-5-enyloxy-phenyl)-5-(5,5,6,6,7,7,8,8,8-nonafluoro-octyloxy)-pyrimidine A solution of DEAD (0.261 g, 1.50 mmol) in THF (20) was added dropwise to a stirred solution of 4-[5-(5,5,6,6,7,7,8,8,8-nonafluorooctyloxy)-pyrimidin-2-yl]-phenol (0.693 g, 1.50 mmol), trans-5-decen-1-ol (0.234 g, 1.50 mmol) and triphenylphosphine (0.399 g, 1.50 mmol) in THF (30) and the reaction mixture stirred at room temperature for 16 h. The solvent was removed in vacuo and the residues purified by column chromatography [silica gel, eluted with hexane/ethyl acetate (4:1)] to yield a colorless solid, which was recrystallized from ethanol.

Yield: 0.47 g, 0.78 mmol, 52%

Transitions: Cr 64.9 SmC 100.4 SmA 102.4 I 1.1 SmA 99.6 SmC 43.3 Cr ° C.

EXAMPLE 4

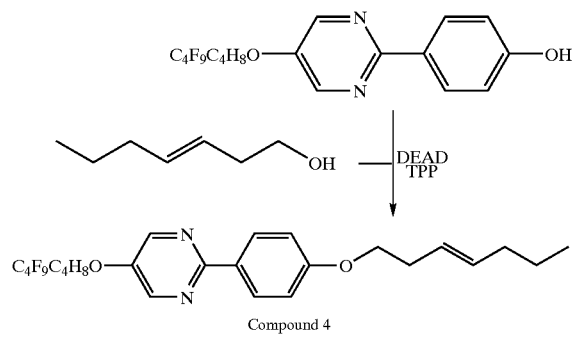

Compound 4

4. Trans-2-(4-Hept-3-enyloxy-phenyl)-5-(5,5,6,6,7,7,8,8,8-nonafluoro-octyloxy)-pyrimidine A solution of DEAD (0.261 g, 1.50 mol) in THF (20) was added dropwise to a stirred solution of 4-[5-(5,5,6,6,7,7,8,8,8-nonafluorooctyloxy)-pyrimidin-2-yl]-phenol (0.693 g, 1.50 mmol), trans-3-hepten-1-ol (0.171 g, 1.50 mmol) and triphenylphosphine (0.399 g, 1.50 mmol) in THF (30) and the reaction mixture stirred at room temperature for 16 h. The solvent was removed in vacuo and the residues purified by column chromatography [silica gel, eluted with hexane ethyl acetate (4:1)] to yield a colorless solid, which was recrystallized from ethanol.

Yield: 0.30 g, 0.54 mmol, 36%

Transitions: Cr 61.7 SmC 135.0 I 134.6 SmC 57.7 Cr ° C.

EXAMPLE 5

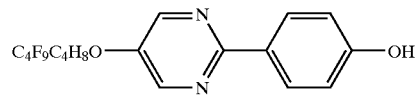

-continued

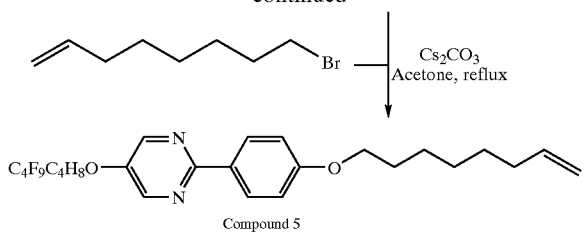

Compound 5

5. 5-(5,5,6,6,7,7,8,8,8-Nonafluoro-octyloxy)-2-(4-oct-7-enyloxy-phenyl)-pyrimidine A suspension of 8-bromo-1-octene (1.00 g, 5.24 mmol), 4-[5-(5,5,6,6,7,7,8,8,8-nonafluorooctyloxy)-pyrimidin-2-yl]-phenol (2.54 g, 5.50 mmol) and cesium carbonate (3.40 g, 10.47 mmol) in acetone (40 ml) was heated under reflux for 12 h, cooled to room temperature, washed with water and the organic layer extracted into ethyl acetate/hexane (3 times). The combined organic extracts were washed with brine, dried (MgSO$_4$) and the solvent removed in vacuo. The residues were purified by column chromatography [silica gel, eluted with hexane/ethyl acetate (9:1)] to yield a colorless solid, which was recrystallized from ethanol.

Yield: 2.79 g, 4.87 mmol, 93%

Transitions: Cr 59.6 SmC 114.2 SmA 121.0 I° C.

Those of ordinary skill in the art will appreciate that compounds, mixtures, methods of synthesis or purification and method of assessing properties of compounds and mixtures other than those specifically described herein can be applied to the practice of this invention. All art-known equivalents of the compounds, mixtures and methods specifically described are encompassed by this invention. All references cited herein are incorporated in their entirety by reference herein to the extent that they are not inconsistent with the disclosure herein.

SCHEME 1

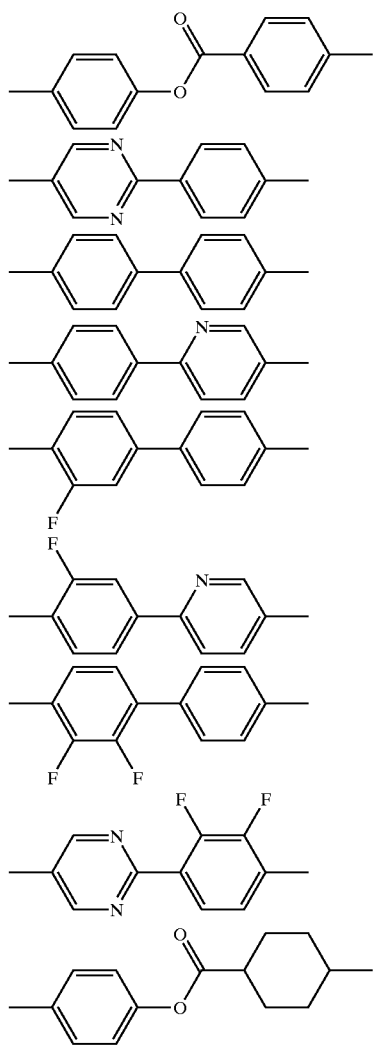

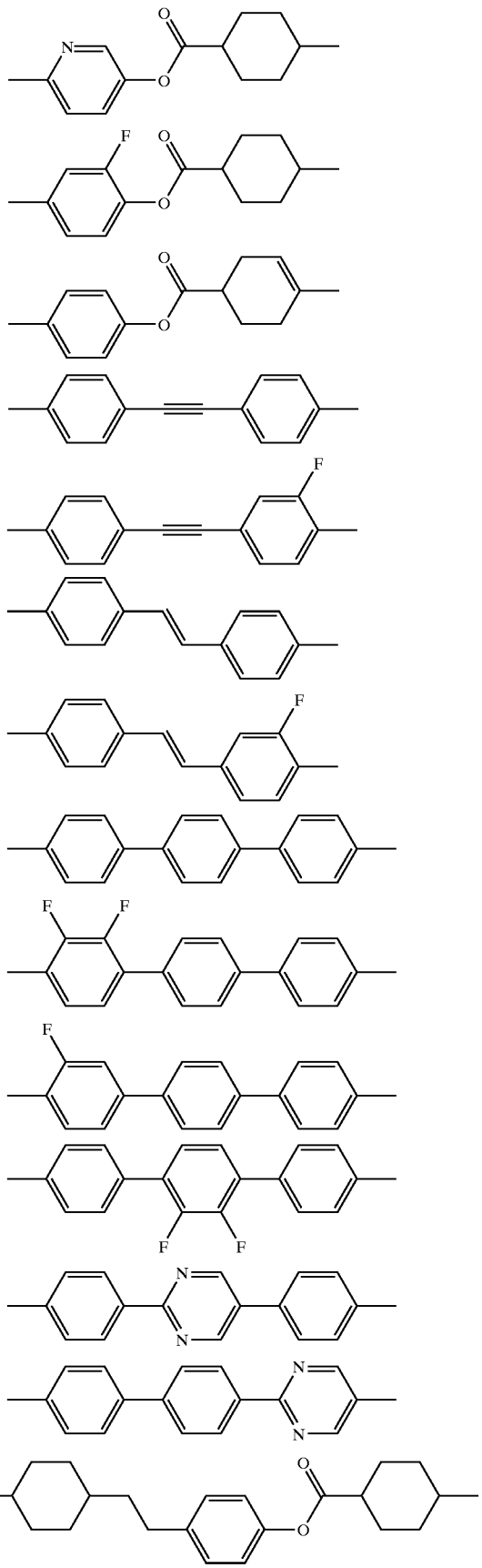

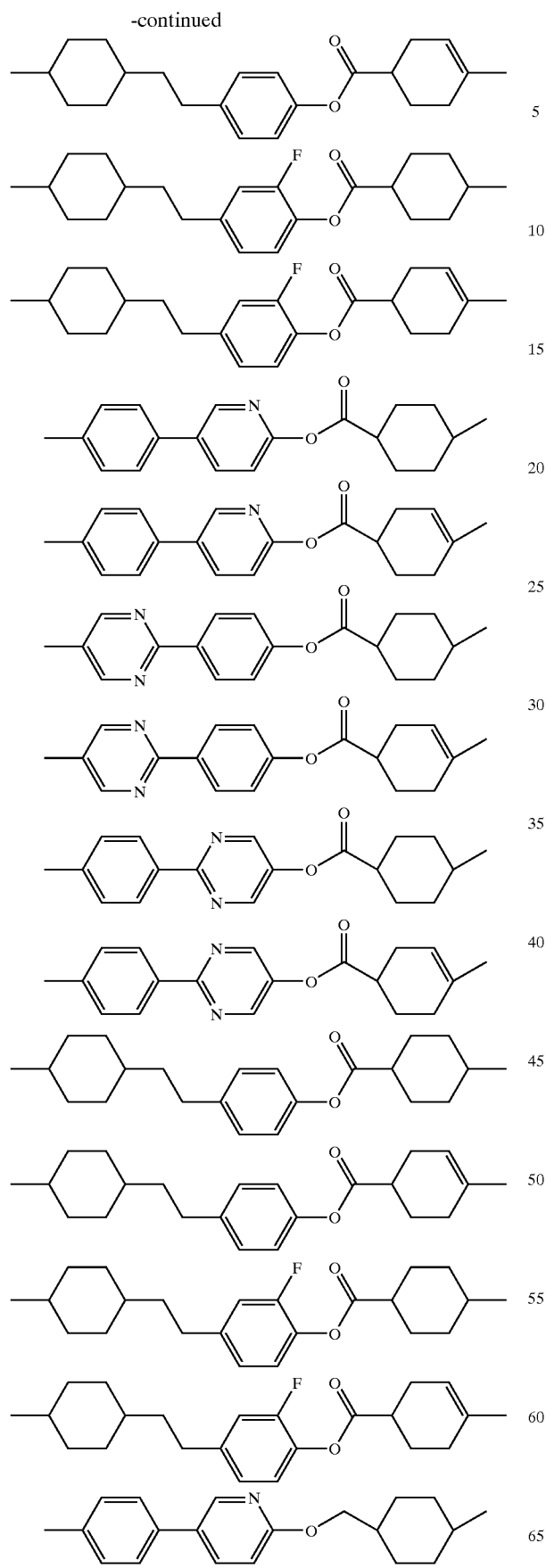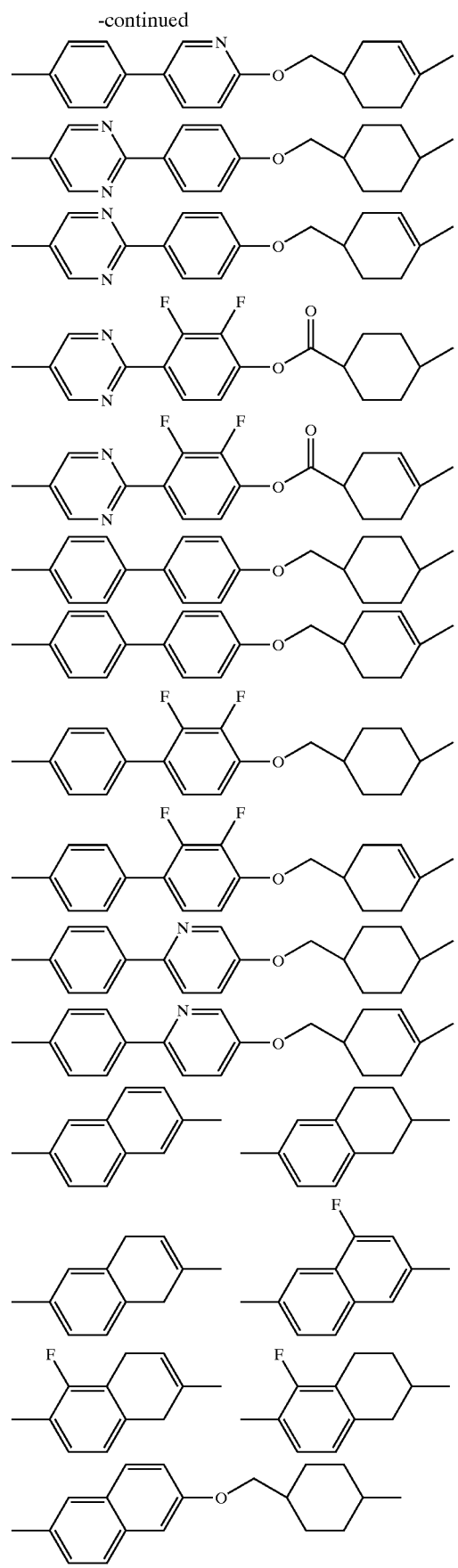

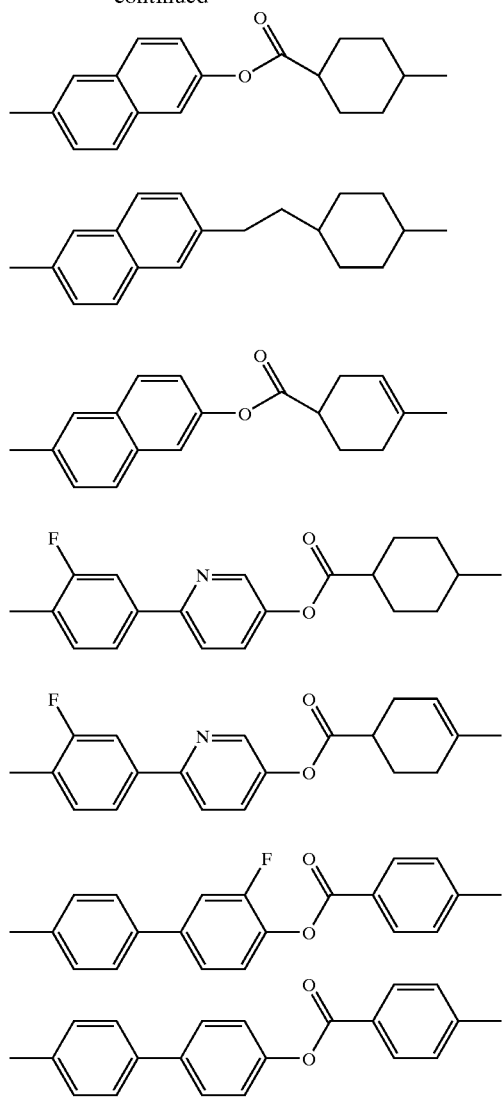
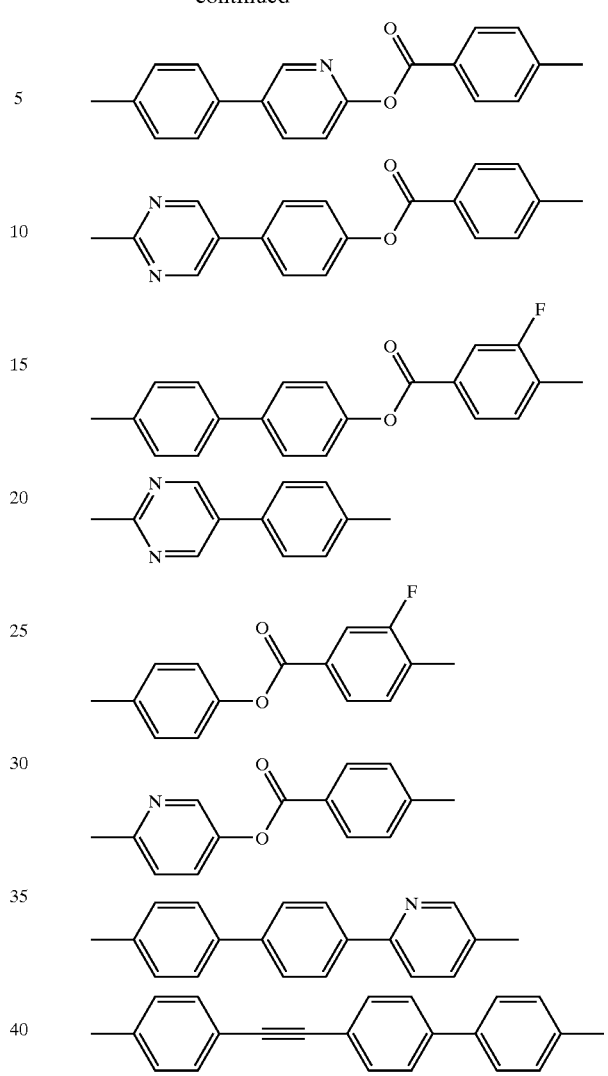
SCHEME 2
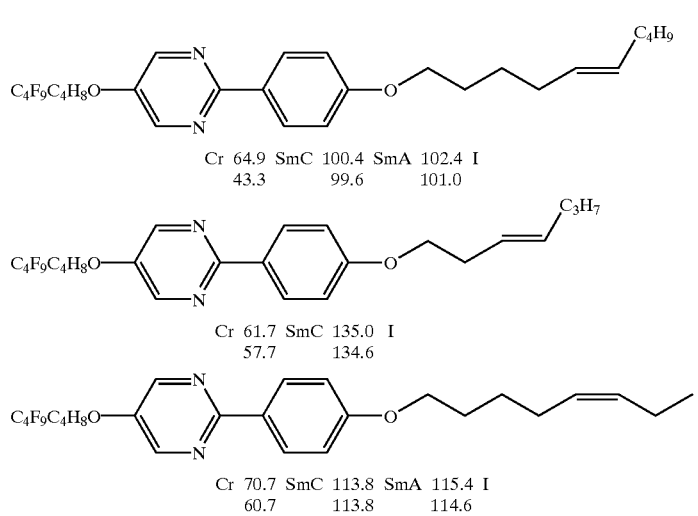

-continued
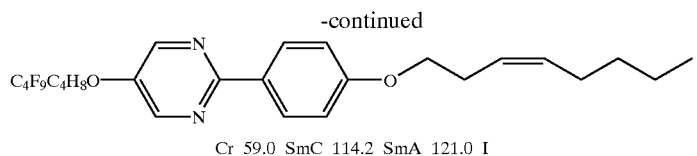
Cr 59.0 SmC 114.2 SmA 121.0 I
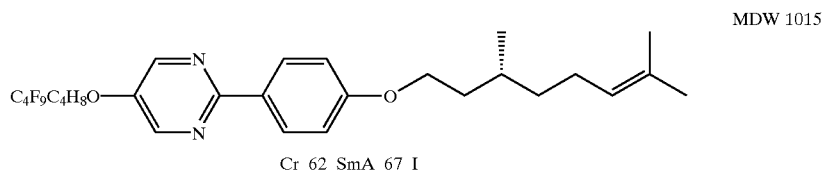
MDW 1015
Cr 62 SmA 67 I
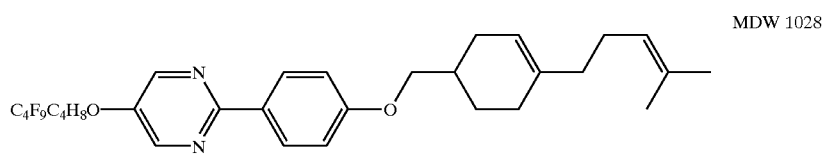
MDW 1028
SCHEME 3
| MDW # | Structure | Phase Diagram |
|---|---|---|
| 950 | 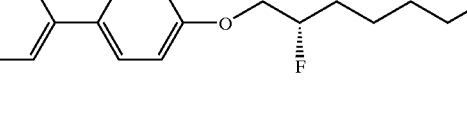 | X<-90-I<br>-94-> |
| 987 | 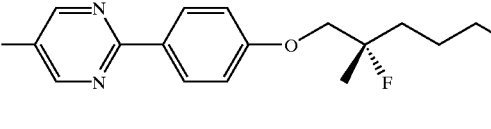 | X<-21-SmC*<-54-SmA<-63-I<br>-53->S?-57-> |
| 644 | 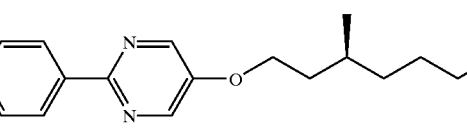 | X<-20-N<-41-I<br>-43->-47-> |
| 699 | 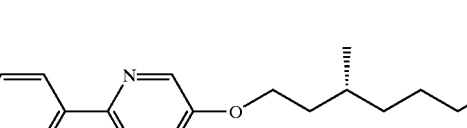 | |
| 139 | 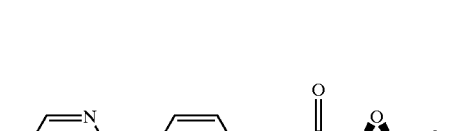 | X-75->I<br><-86- |

-continued
SCHEME 3
| MDW # | Structure | Phase Diagram |
|---|---|---|
| 31 | 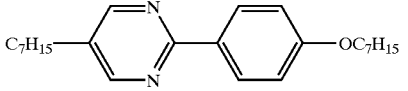 | |
| 3 | 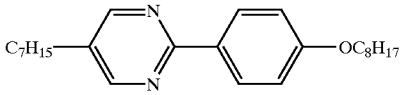 | X-49->A-44->N-69.5->I |
| 1695 | 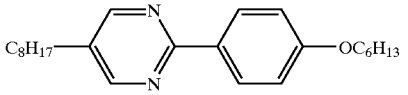 | |
| 5 | 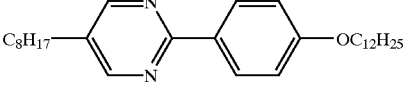 | X-43.2->C-62.4->A-66.8->N -68.2->I |
| 4 | 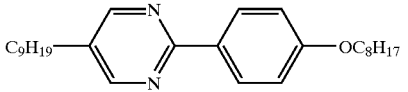 | X-33->C-60->A-74.5->I |
| 913 | 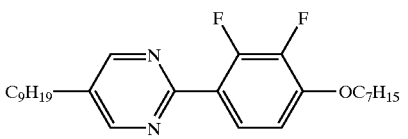 | X-43->C-50->I <-44-<52- |
| 911 | 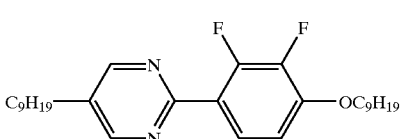 | X-44->C-52->I <-37-<-52- |
| 374 | 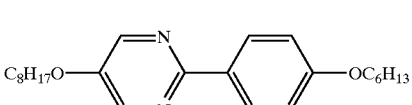 | |

-continued

SCHEME 3

| MDW # | Structure | Phase Diagram |
|---|---|---|
| 337 | 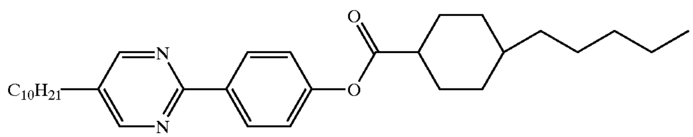 | X<-100-C<-105-N<-169-I |
| 1135 | 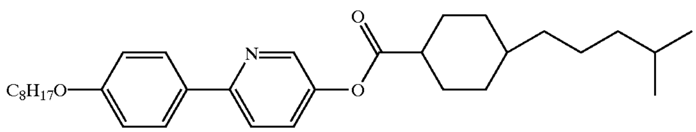 | X<-73.5-S?<-85-C<br><-104-A<-175-N<br><-186-I |
| 1638 | 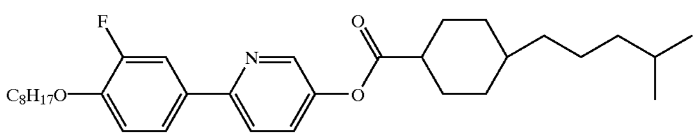 | |
| 1458 | 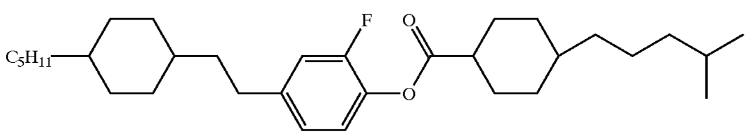 | |
| 1671 | 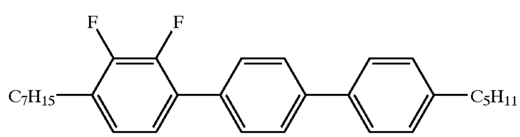 | X-56->C-106-><br>A-131->N-136->I |
| 1673 | 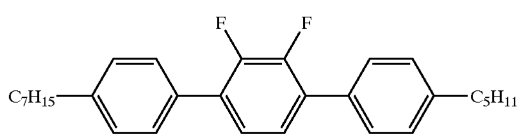 | X-37->N-112->I<br>X<-24-C |
| 1674 | 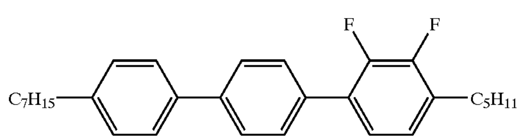 | X-66->SI-75->C-119-><br>A-135->N-137->I |
| 1054 | 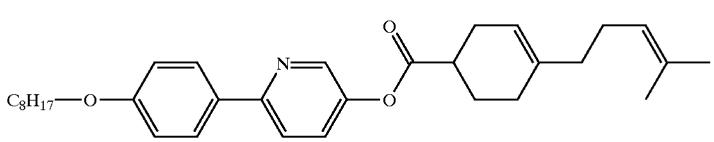 | X<-C<-135-N<-150-I<br>-55->Sx-82-> |
| 942 | 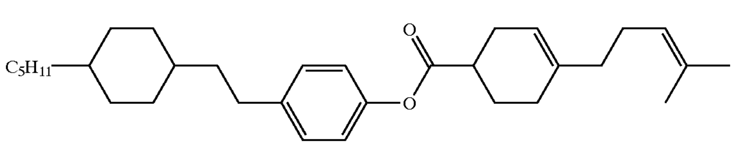 | |

SCHEME 3

| MDW # | Structure | Phase Diagram |
|---|---|---|
| 576 | 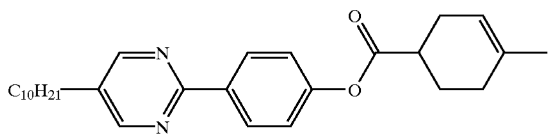 | X<-35-S?<-45-C<-68-N<-107-I -50->-54-> |
| 1059 | 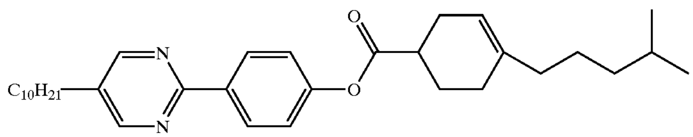 | |
| 336 | 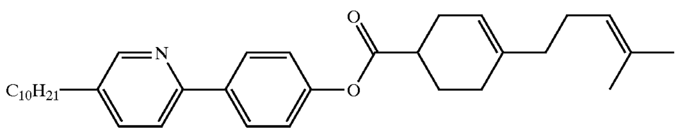 | X<-27-C<-83-N<-106-I -40-> |
| 577 | 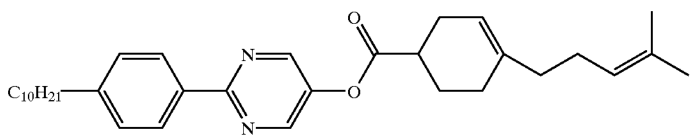 | |
| 1701 | 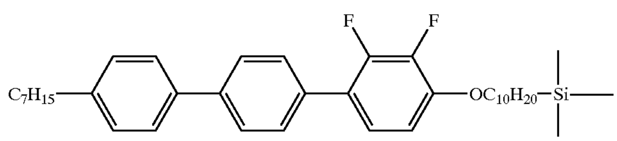 | |
| 1658 | 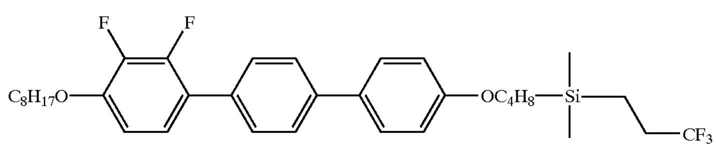 | |
| 1592 | 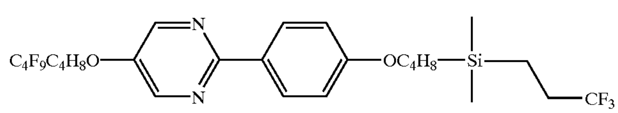 | |
| 1532 | 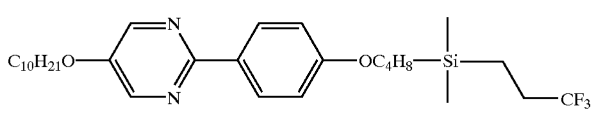 | |
| 1632 | 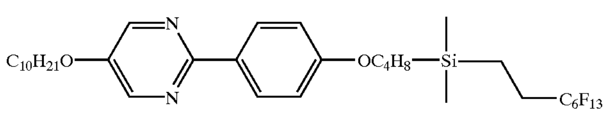 | |
| 1586 | 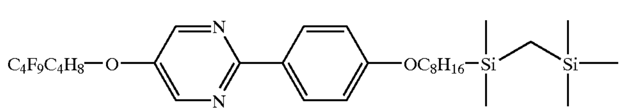 | |
| 1709 | 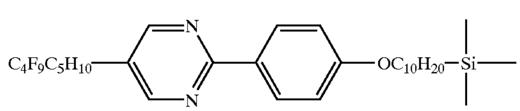 | |

SCHEME 4
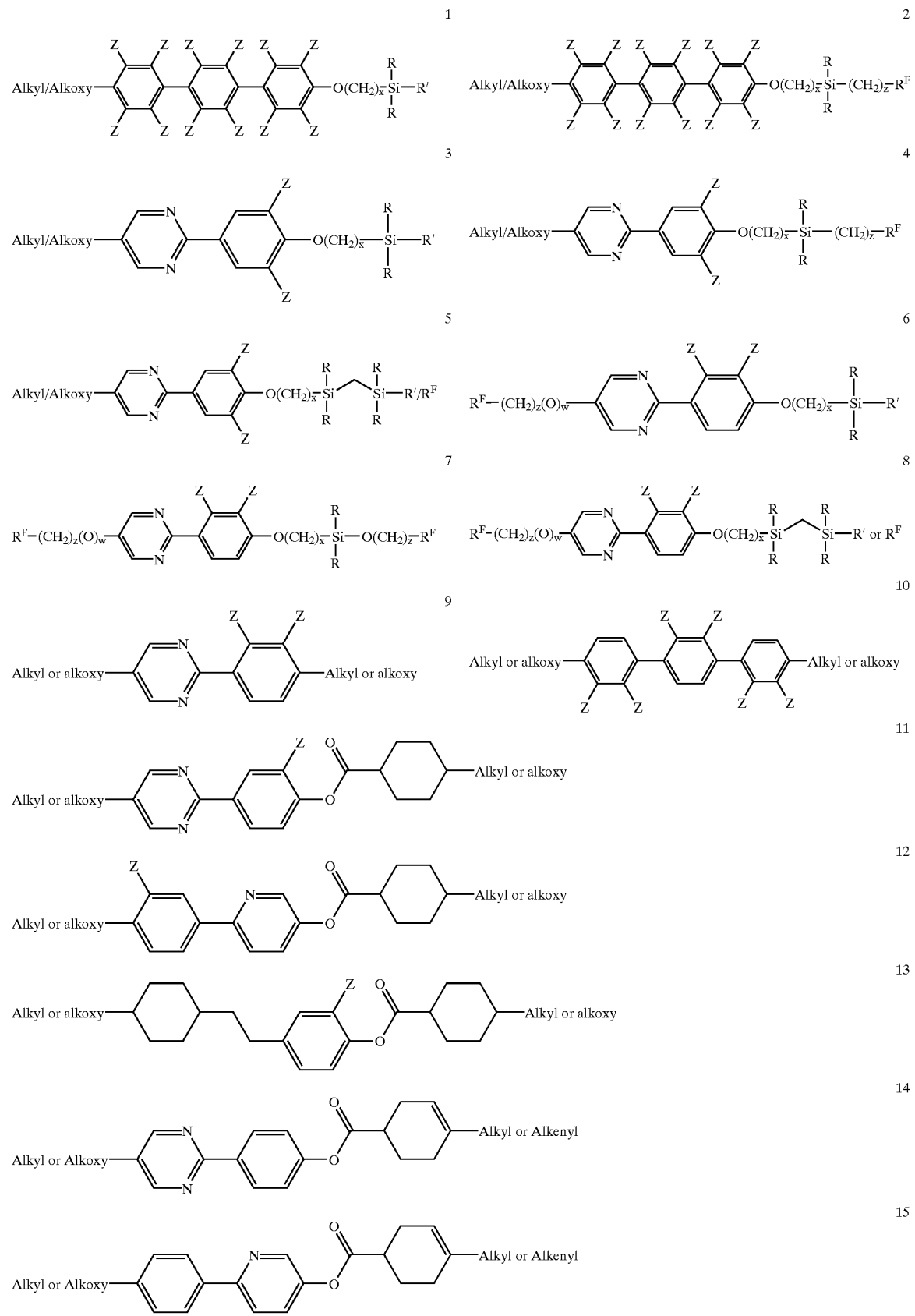

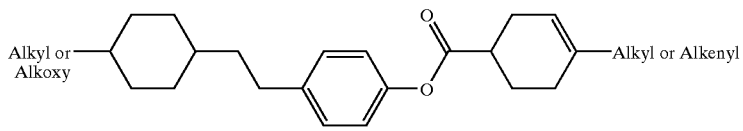

16

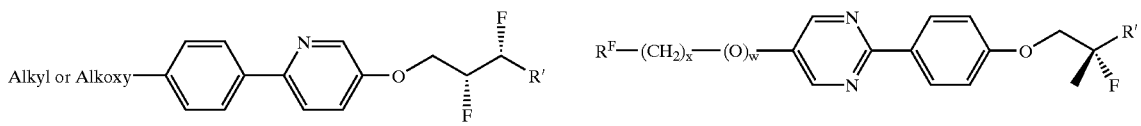

17

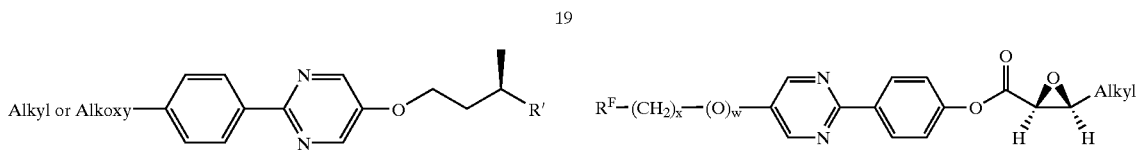

18

19

20 wherein x and z are integers ranging from 1 to 20; w is 0 or 1; R is an alkyl group preferably having from 1 to 6 carbon atoms; R' is an alkyl group having from 5 to 20 carbon atoms; $R^F$ is a perfluoroalkyl group; Z is H or a F; and alkyl or alkoxy groups are those that have 5 to 20 carbon atoms.

TABLE 1

| MX # | PS | Visc | E rise | Resistivity | Dielec | Applied Fi | Phase diagram | DSC MP | DSC FP |
|---|---|---|---|---|---|---|---|---|---|
| | | | | APT data | | | Phase info | | |
| 9244 | 27.8 | 88.9 | 127 | | | | I - 107.6 - N - 98.6 - A - 86.3 - C | -25.9 | -60 |
| 9295 | 24 | 73 | 130 | | | | I - 102.2 - N - 96.8 - A - 82.8 - C | -30.5 | <-25 |
| 9338 | | | | | | | I - 106.9 - N - 96.0 - A - 78.8 - C | 2.2 | -29.3 |
| 9365 | 33.31 | 162.8 | 130 | | 4.39 | | I - 110.0 - N - 103.8 - A - 93.7 - C | -2.2 | -29.4 |
| 9405 | 14.4 | 70.9 | 207 | 3.1 e+11 | 3.92 | 6 | I - 103.8 - N - 100.1 - A - 85.1 - C | -43.1 | -60 |
| 9417 | 19.5 | 80.3 | 162 | 1.4 e+11 | 3.97 | 6 | I - 102.9 - N - 98.0 - A - 92.2 - C - -28.9 - Sx | -34.9 | -60 |
| 9426 | 29.4 | 195.7 | 145 | 9.5 e+10 | 4.37 | 6 | I - 104.2 - N - 102.3 - A - 90.2 - C | -35.7 | -60 |
| 9427 | 35.4 | 96.4 | 115 | 3.6 e+11 | 4.52 | 6 | I - 102.1 - N - 95.8 - A - 90.2 - C | -56.4 | -60 |
| 9435 | 33.9 | 89.9 | 112 | 1.8 e+11 | 4.66 | 6 | I - 100.0 - N - 94.6 - A - 87.3 - C | -47.4 | -60 |
| 9441 | | | | | | | | | |
| 9451 | 14.7 | 61.2 | 57 | 3.7 E+11 | 3.34 | 6.83 | I - 82.1 - A - 74.6 - C | -16.6 | -23.3 |
| 9452 | 16.28 | 106.94 | 112 | | 3.37 | 6 | I - 82.1 - A - 74.6 - C | -26.4 | -29.2 |
| 9454 | 35.1 | 92.2 | 110 | 3.8 e+11 | 3.88 | 6 | I - 114.0 - N - 93 - A - 90.8 - C | -32.4 | -60 |

TABLE 2

| | Physical Data | |
|---|---|---|
| | MX 9244 | MX 9295 |
| PS | 27.8 | 24 |
| Vis | 88.9 | 73 |
| E Rise | 127 | 130 |
| DC | 4.58 | 4.11 |
| I to N | 107.6 | 102.2 |
| N to A © | 98.6 | 96.8 |
| A to C © | 86.3 | 82.8 |
| C to X © | >-25 | >-25 |
| X to C © | -25.9 | -30.5 |
| Ne | 1.613 | 1.613 |
| No | 1.47 | 1.473 |
| Delta N | 0.143 | 0.14 |

TABLE 2-continued

| | Optical Response | | | | | |
|---|---|---|---|---|---|---|
| | Rise time | fall time | Tilt angle | Rise time | fall time | Tilt angle |
| 1.65 V | | | | | | |
| -10 | 5.77 ms | 12.9 ms | 19.9 | | | |
| 5 | 1.91 ms | 2.34 ms | 19.7 | | | |
| 62 | .077 ms | 0.08 | 17.8 | | | |
| 2.5 V | | | | | | |
| 30 | | | | .155 ms | .164 ms | 20.3 |
| 35 | | | | .122 ms | .132 ms | 20 |
| 40 | | | | .074 ms | .082 ms | 19.4 |

TABLE 3
MX number 9244
| Component | Percent | Structure | Phase diagram |
|---|---|---|---|
| MDW 950 | 2.00 | 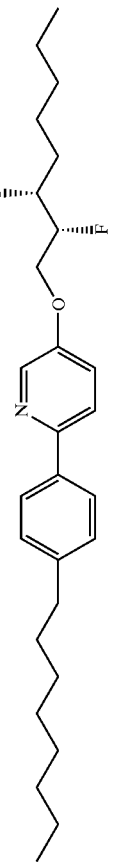 | I - 90 -> X; X - 94 -> I |
| MDW 987 | 16.00 | 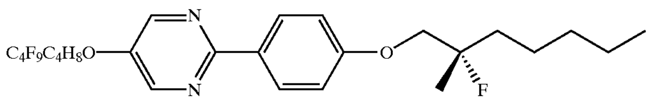 | I - 63 -> A - 54 -> C* - 21 -> X; X - 53 -> S? - 57 -> C* |
| MDW 1458 | 10.50 | 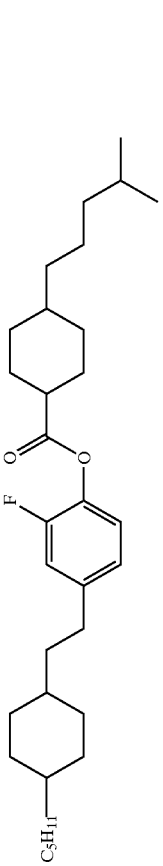 | |
| MDW 913 | 6.00 | 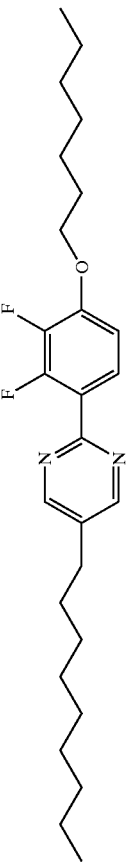 | I - 50 -> C - 32 -> X; X - 43 -> C - 50 -> I |
| MDW 911 | 6.00 | 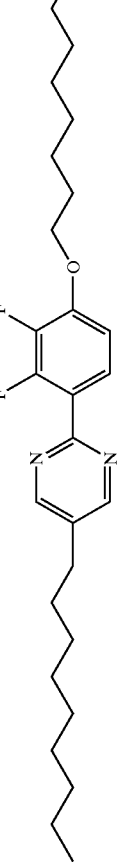 | I - 52 -> C - 37 -> X; X - 44 -> C - 52 -> I |
| MDW 374 | 10.00 | 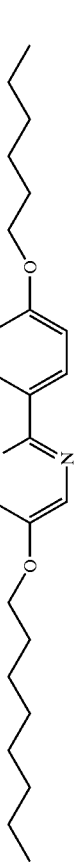 | |

TABLE 3-continued
MX number 9244
| Component | Percent | Structure | Phase diagram |
|---|---|---|---|
| MDW 337 | 18.00 | 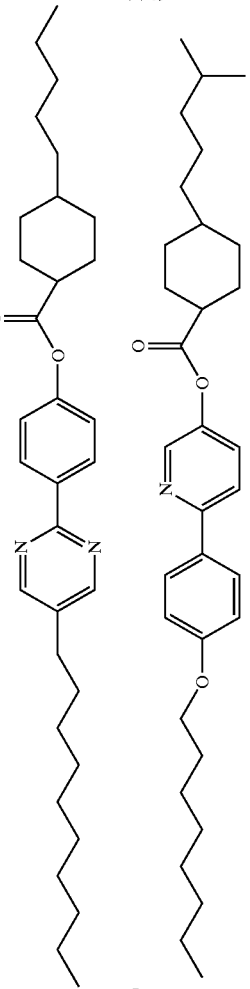 | I - 169 -> N - 105 -> C - 100 -> X; |
| MDW 1135 | 13.50 | 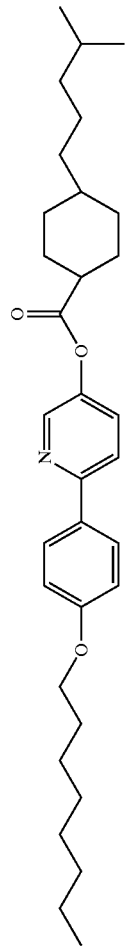 | I - 186 -> N - 175 -> A - 104 -> C - 85 -> S? -> X; S? < 73.5 - X |
| MDW 1592 | 3.00 | 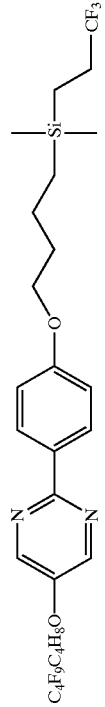 | X -> 69.2 -> I; I -> 55.9 -> X |
| MDW 1632 | 3.00 | 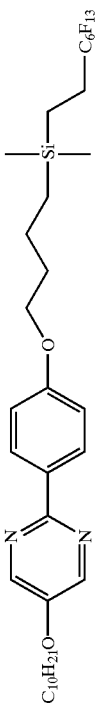 | X 41.1 C 86.1 A 101.3 I 99.6 A 84.8 C |
| MDW 4 | 3.00 | 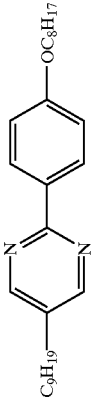 | X - 33 - C - 60 - A - 74.5 - I; |

TABLE 3-continued

MX number 9244

| Component | Percent | Structure | Phase diagram |
|---|---|---|---|
| MDW 5 | 3.00 | C$_8$H$_{17}$—[pyrimidine]—[phenyl]—OC$_{12}$H$_{25}$ | X - 43.2 - C 62.4 A - 66.8 - N - 68.2 - I; |
| MDW 31 | 3.00 | C$_7$H$_{15}$—[pyrimidine]—[phenyl]—OC$_7$H$_{15}$ | |
| MDW 1671 | 3.00 | [pentyl-biphenyl-difluorophenyl-heptyl structure] | X - 56 -> C - 106 -> A - 131 -> N - 136 -> I |

TABLE 4

MX number 9295

| MDW Component | Percent | Structure | Phase diagram |
|---|---|---|---|
| 950 | 2.00 | 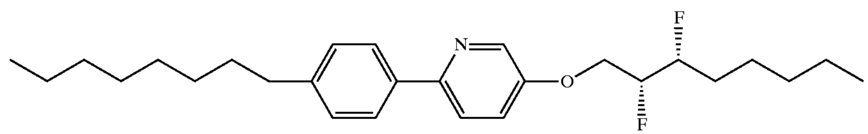 | I - 90 -> X; X - 94 -> I |
| 987 | 16.00 | 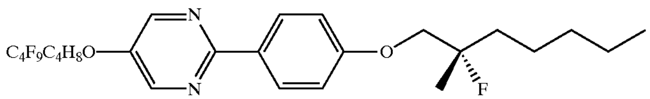 | I - 63 -> A - 54 -> C* - 21 -> X; X - 53 -> S? - 57 -> C* |
| 374 | 8.00 | 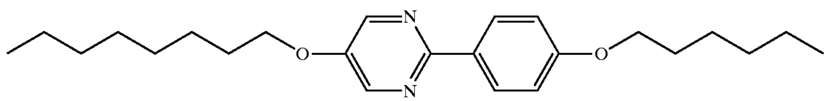 | I - 50 -> C - 32 -> X; X - 43 -> C - 50 -> I |
| 913 | 4.00 | 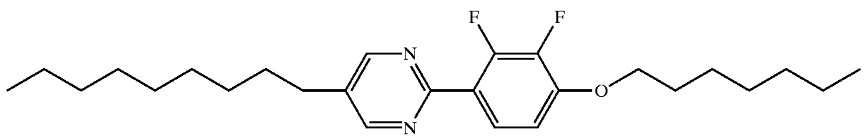 | X 41.1 C 86.1 A 101.3 I 99.6 A 84.8 C |
| 1632 | 3.00 | 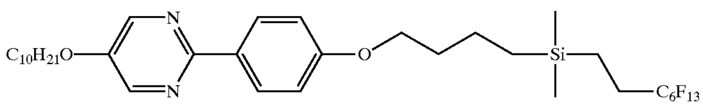 | X - 48 -> C - 86 -> A - 90 -> I; C - 42 -> SI - 25 -> X |
| 1586 | 3.00 | 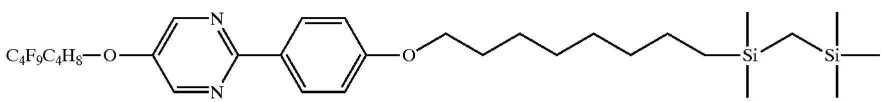 | |
| 337 | 18.00 | 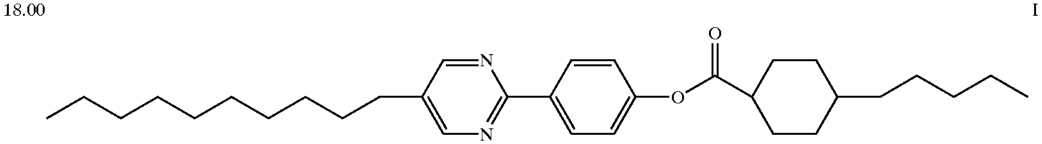 | I - 169 -> N - 105 -> C - 100 -> X; |

TABLE 4-continued

MX number 9295

| MDW Component | Percent | Structure | Phase diagram |
|---|---|---|---|
| 1135 | 8.00 | 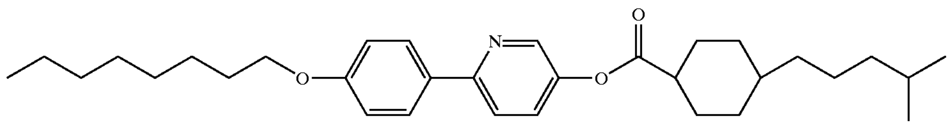 | I - 186 -> N - 175 -> A - 104 -> C - 85 -> S? -> X; S? <- 73.5 - X |
| 1598 | 4.00 | 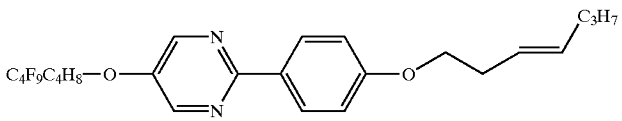 | |
| 1673 | 3.00 | 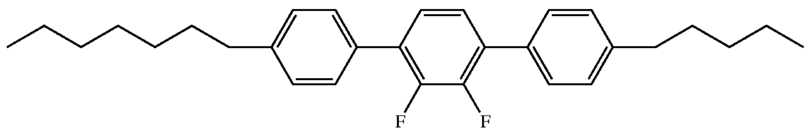 | X - 37 -> N - 112 -> I; C - 24 -> X |
| 1458 | 10.00 | 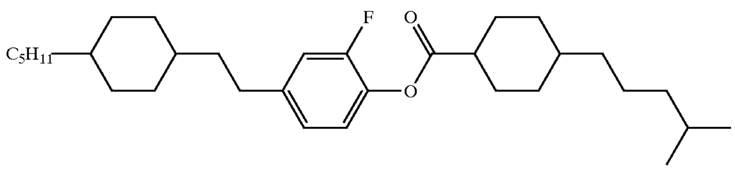 | |
| 3 | 7.00 | 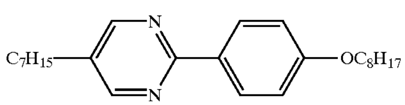 | X - 49 - A - 44 - N - 69.5 - I; |
| 4 | 7.00 | 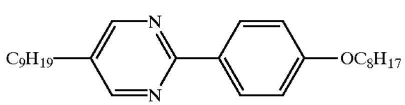 | X - 33 - C - 60 - A - 74.5 - I; |
| 5 | 7.00 | 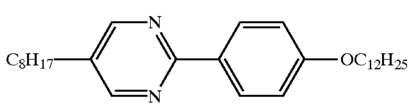 | X - 43.2 - C 62.4 A - 66.8 - N - 68.2 - I; |

TABLE 5
MX number 9338
| Component | Percent | Structure | Phase diagram |
|---|---|---|---|
| 1597 | 5.56 | 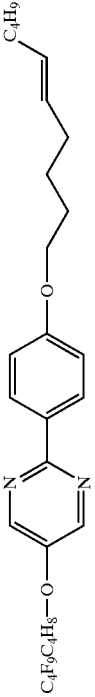 | |
| 1598 | 5.56 | 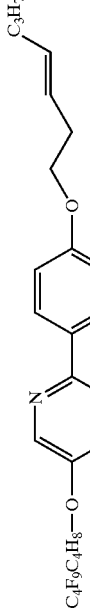 | I - 63 -> A - 54 -> C* - 21 -> X; X - 53 -> S? - 57 -> C* |
| 987 | 15.56 | 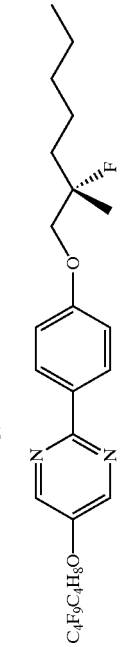 | I - 90 -> X; X - 94 -> I |
| 950 | 4.44 | 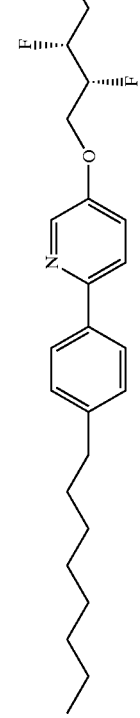 | I - 41 -> N - 20 -> X; X - 43 -> N - 47 -> I |
| 644 | 2.22 | 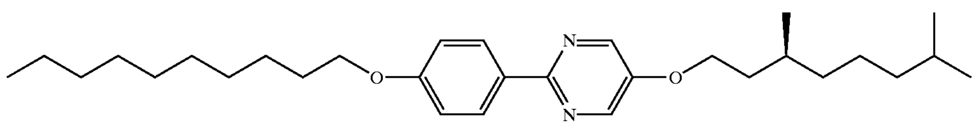 | X - 37 -> N - 112 -> I; C - 24 -> X |
| 1673 | 11.11 | 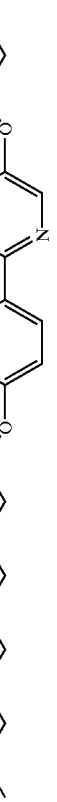 | X - 56 -> C - 106 -> A - 131 -> N - 136 -> I |
| 1671 | 4.44 | 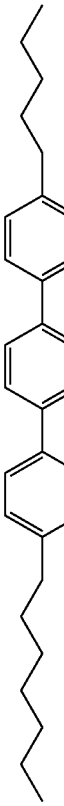 | |

TABLE 5-continued

MX number 9338

| Component | Percent | Structure | Phase diagram |
|---|---|---|---|
| 1674 | 4.44 | 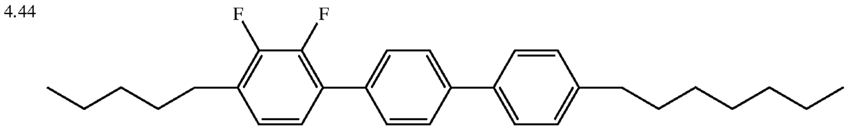 | X - 66 -> SI - 75 -> C - 119 -> A - 135 -> N - 137 -> I |
| 1701 | 8.89 | 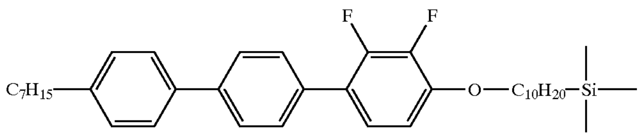 | I - 169 -> N - 105 -> C - 100 -> X; Q |
| 337 | 24.44 | 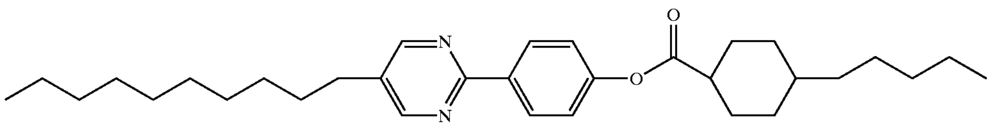 | Q; Q |
| 374 | 3.33 | 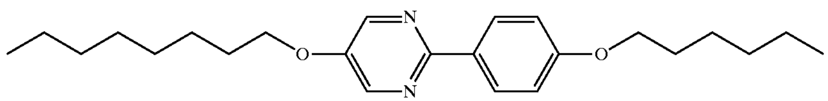 | |
| 5 | 3.33 | 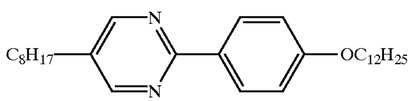 | K - 43.2 - C 62.4 A - 66.8 - N - 68.2 - I; Q |
| 1695 | 6.67 | 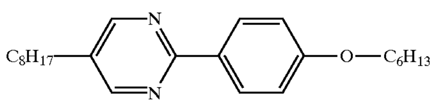 | |

TABLE 6
9365
| Component | Percent | Structure | Phase diagram |
|---|---|---|---|
| 544 | 2.00 | 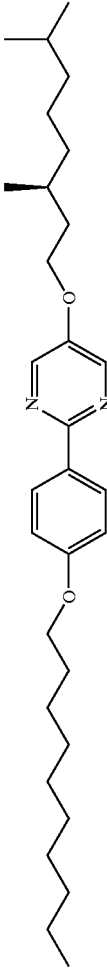 | I - 41 -> N - 20 -> X; X - 43 -> N - 47 -> I |
| 950 | 3.00 | 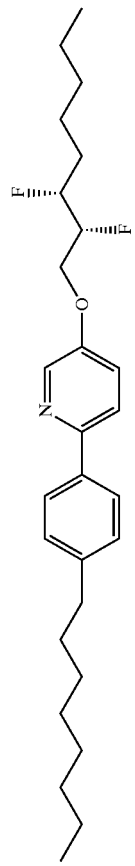 | I - 90 -> X; X - 94 -> I |
| 987 | 10.00 | 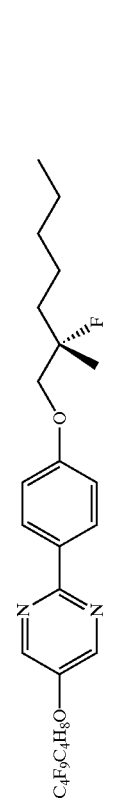 | I - 63 -> A - 54 -> C* - 21 -> X; X - 53 -> S? - 57 -> C* |
| 1673 | 15.00 | 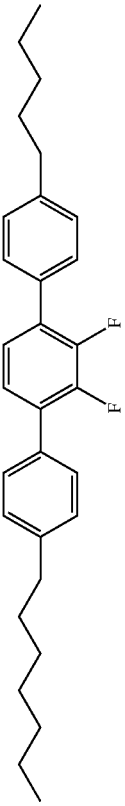 | X - 37 -> N - 112 -> I; C - 24 -> X |
| 1597 | 10.00 | 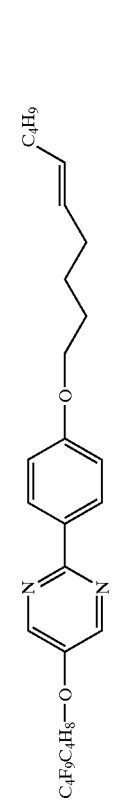 | |
| 337 | 20.00 | 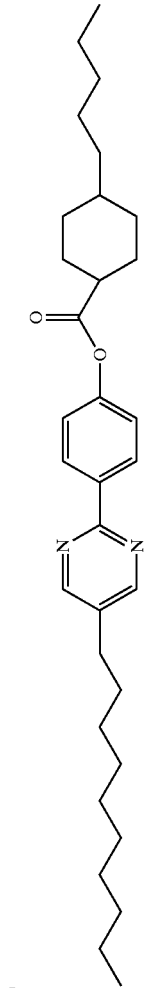 | I - 169 -> N - 105 -> C - 100 -> X; |
| 1701 | 10.00 | 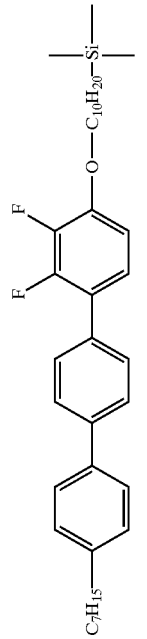 | |

TABLE 7

MX number 9405

| Component | Percent | Structure | Phase diagram |
|---|---|---|---|
| 699 | 1.94 | 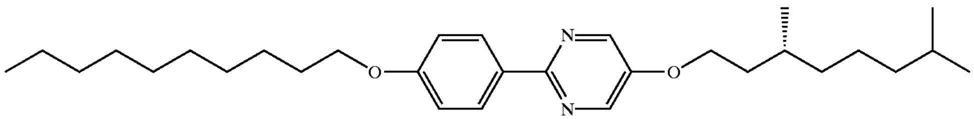 | |
| 987 | 13.81 | 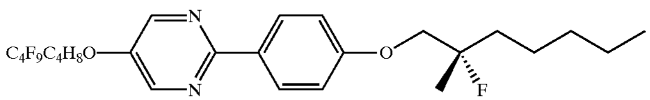 | I - 63 -> A - 54 -> C* - 21 -> X; X - 53 -> S? - 57 -> C* |
| 374 | 10.19 | 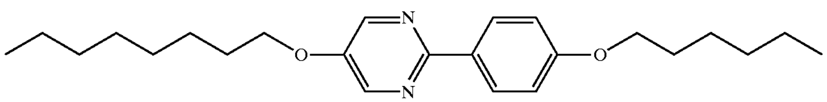 | |
| 1586 | 7.14 | 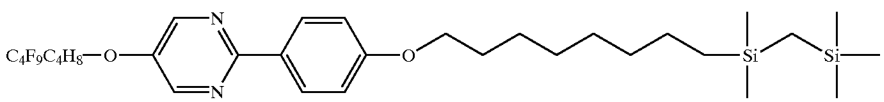 | X - 48 -> C - 86 -> A - 90 -> I; C - 42 -> SI - 25 -> X |
| 337 | 20.11 | 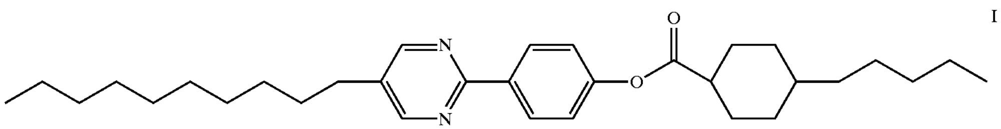 | I - 169 -> N - 105 -> C - 100 -> X; Q |
| 1638 | 7.71 | 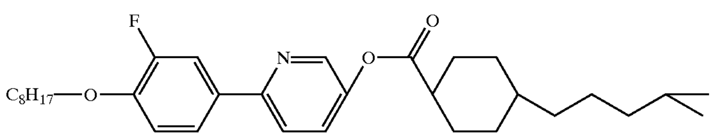 | |
| 1598 | 5.96 | 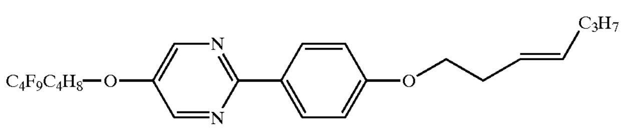 | |

TABLE 7-continued
MX number 9405
| Component | Percent | Structure | Phase diagram |
|---|---|---|---|
| 1673 | 2.99 | 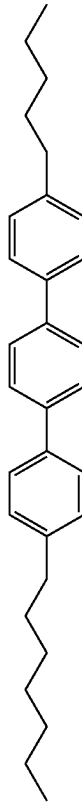 | X - 37 -> N - 112 -> I; C - 24 -> X |
| 1458 | 9.82 | 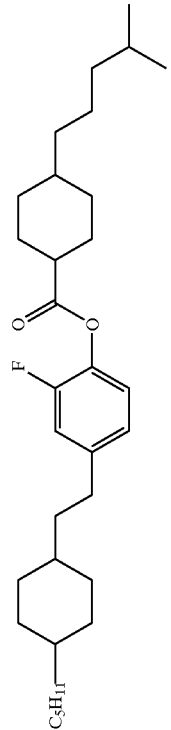 | X - 43.2 - C 62.4 A - 66.8 - N - 68.2 - I; |
| 5 | 13.56 | 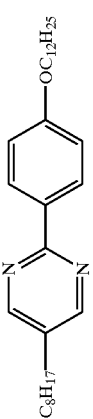 | |
| 1695 | 6.76 | 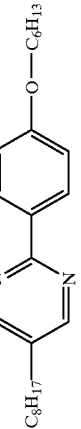 | |
| | 0.00 | | |
| | 0.00 | | |
| | 0.00 | | |
| | 0.00 | | |
| | 0.00 | | |

TABLE 8

MX number 9417

| Component | Percent | Structure | Phase diagram |
|---|---|---|---|
| 1598 | 20.00 | [structure: C₄F₉C₄H₈O-phenyl-pyrimidine-O-CH₂CH=CHCH₂-C₃H₇] | I - 63 -> A - 54 -> C* - 21 -> X; X - 53 -> S? - 57 -> C* |
| 987 | 12.00 | [structure: C₄F₉C₄H₈O-phenyl-pyrimidine-O-CH₂-C(F)(CH₃)-C₅H₁₁] | I - 90 -> X; X - 94 -> I |
| 950 | 1.50 | [structure: C₇H₁₅-phenyl-pyridine-O-CH₂-CHF-CHF-C₅H₁₁] | |
| 1673 | 7.00 | [structure: C₇H₁₅-biphenyl-difluorophenyl-C₇H₁₅] | X - 37 -> N - 112 -> I; C - 24 -> X |
| 1671 | 4.00 | [structure: C₇H₁₅-biphenyl-difluorophenyl-C₇H₁₅] | X - 56 -> C - 106 -> A - 131 -> N - 136 -> I |

TABLE 8-continued

MX number 9417

| Component | Percent | Structure | Phase diagram |
|---|---|---|---|
| 1674 | 4.00 | 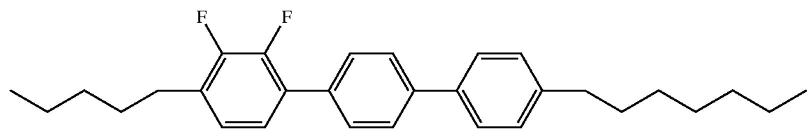 | X - 66 -> SI - 75 -> C - 119 -> A - 135 -> N - 137 -> I |
| 337 | 25.00 | 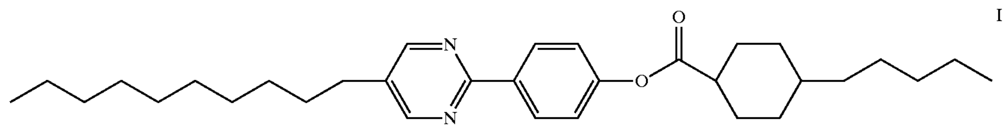 | I - 169 -> N - 105 -> C - 100 -> X; |
| 374 | 13.50 | 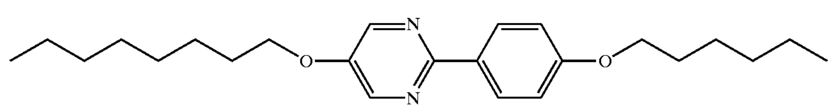 | |
| 5 | 13.00 | 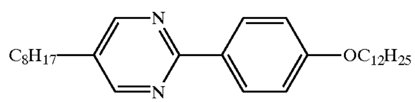 | X - 43.2 - C 62.4 A - 66.8 - N - 68.2 - I; |

TABLE 9

MX number 9426

| Component | Percent | Structure | Phase diagram |
|---|---|---|---|
| 1598 | 7.17 | 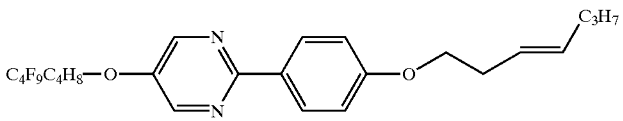 | I - 63 -> A - 54 -> C* - 21 -> X; X - 53 -> S? - 57 -> C* |
| 987 | 18.25 | 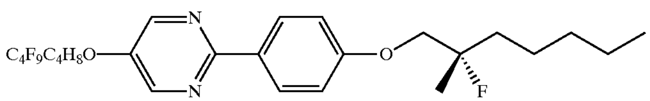 | I - 90 -> X; X - 94 -> I |
| 950 | 2.28 | 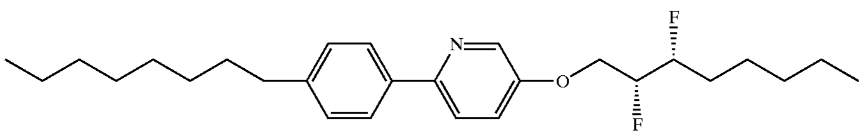 | |
| 1673 | 7.19 | 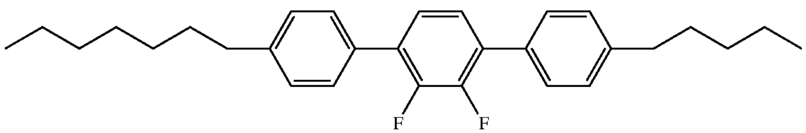 | X - 37 -> N - 112 -> I; C - 24 -> X |
| 1671 | 4.08 | 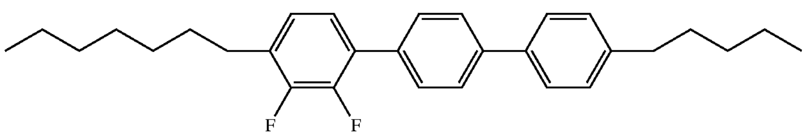 | X - 56 -> C - 106 -> A - 131 -> N - 136 -> I |

TABLE 9-continued

MX number 9426

| Component | Percent | Structure | Phase diagram |
|---|---|---|---|
| 1674 | 4.13 | 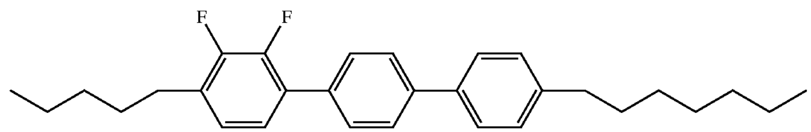 | X - 66 -> SI - 75 -> C - 119 -> A - 135 -> N - 137 -> I |
| 337 | 26.18 | 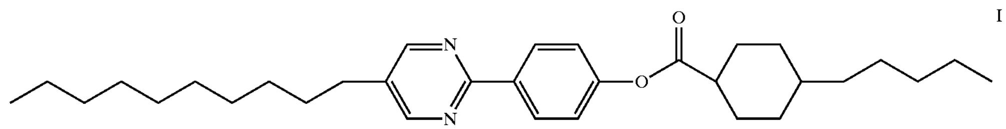 | I - 169 -> N - 105 -> C - 100 -> X; |
| 374 | 10.22 | 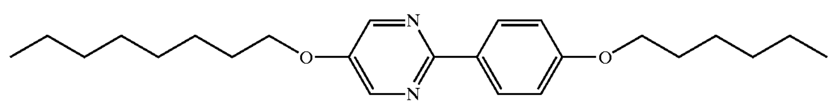 | |
| 5 | 7.42 | 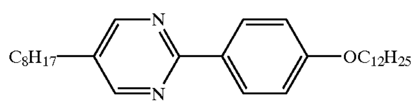 | X - 43.2 - C 62.4 A - 66.8 - N - 68.2 - I; |
| 1586 | 5.93 | 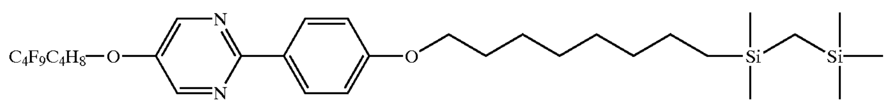 | |
| 1597 | 7.15 | 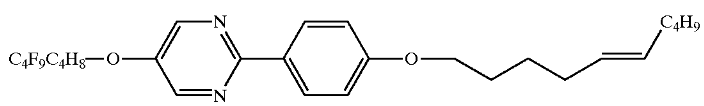 | X - 48 -> C - 86 -> A - 90 -> I; C - 42 -> SI - 25 -> X |

TABLE 10

MX number 9427

| Component | Percent | Structure | Phase diagram |
|---|---|---|---|
| 1597 | 5.56 | C₄F₉C₄H₈—O—⟨phenyl⟩—⟨pyrimidine⟩—O—CH₂CH=CH—C₄H₉ | |
| 1598 | 5.56 | C₄F₉C₄H₈—O—⟨phenyl⟩—⟨pyrimidine⟩—O—CH₂CH=CH—C₃H₇ | |
| 987 | 15.56 | C₄F₉C₄H₈O—⟨phenyl⟩—⟨pyrimidine⟩—OCH₂C*(F)(CH₃)C₅H₁₁ | I - 63 -> A - 54 -> C* - 21 -> X; X - 53 -> S? - 57 -> C* |
| 950 | 4.17 | ⟨pyridine-phenyl⟩ with OCH₂CHF-CHF-C₅H₁₁ and C₉H₁₉ chain | I - 90 -> X; X - 94 -> I |
| 644 | 3.33 | ⟨pyrimidine-phenyl⟩ with O-CH₂CH₂C*H(CH₃)CH₂CH(CH₃)₂ and OC₉H₁₈... | I - 41 -> N - 20 -> X; X - 43 -> N - 47 -> I |
| 1673 | 11.11 | C₅H₁₁—⟨phenyl⟩—⟨phenyl⟩—⟨difluorophenyl⟩—C₇H₁₅ | X - 37 -> N - 112 -> I; C - 24 -> X |
| 1671 | 4.44 | C₅H₁₁—⟨phenyl⟩—⟨phenyl⟩—⟨difluorophenyl⟩—C₇H₁₅ | X - 56 -> C - 106 -> A - 131 -> N - 136 -> I |

TABLE 10-continued
MX number 9427
| Component | Percent | Structure | Phase diagram |
|---|---|---|---|
| 1674 | 4.44 | 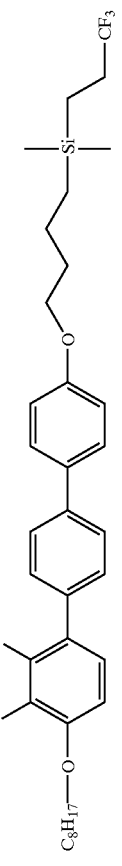 | X - 66 -> SI - 75 -> C - 119 -> A - 135 -> N - 137 -> I |
| 1658 | 8.89 | 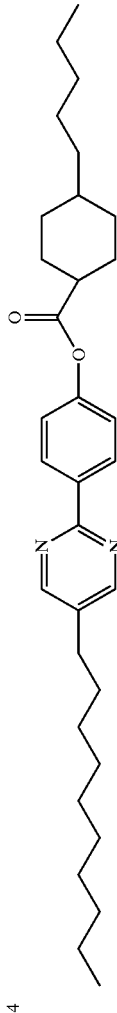 | I 128.4 -> C - 37.5 -> X; X - 41 -> C |
| 337 | 24.44 | 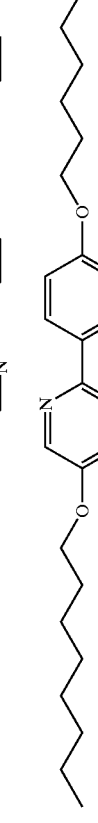 | I - 169 -> N - 105 -> C - 100 -> X; |
| 374 | 3.33 | 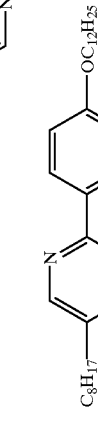 | |
| 5 | 3.33 | 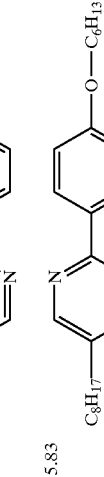 | X - 43.2 - C 62.4 A - 66.8 - N - 68.2 - I; |
| 1695 | 5.83 | 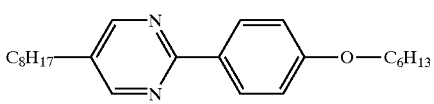 | |

TABLE 11

MX number 9435

| Component | Percent | Structure | Phase diagram |
|---|---|---|---|
| 950 | 4.00 | 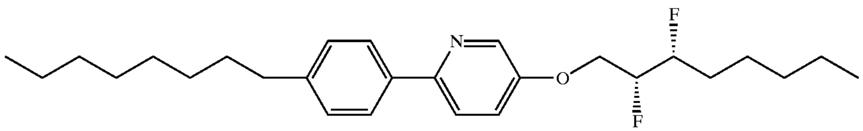 | I - 90 -> X; X - 94 -> I |
| 987 | 15.00 | 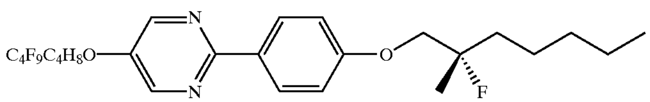 | I - 63 -> A - 54 -> C* - 21 -> X; X - 53 -> S? - 57 -> C* |
| 644 | 3.00 | 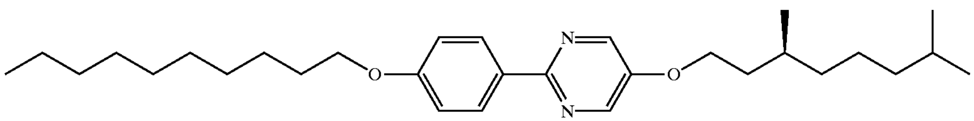 | I - 41 -> N - 20 -> X; X - 43 -> N - 47 -> I |
| 1673 | 10.00 | 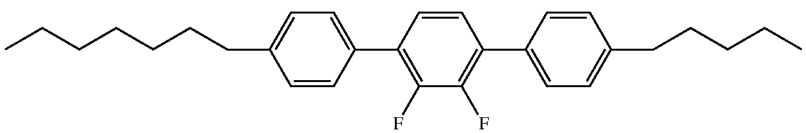 | X - 37 -> N - 112 -> I; C - 24 -> X |
| 1671 | 5.00 | 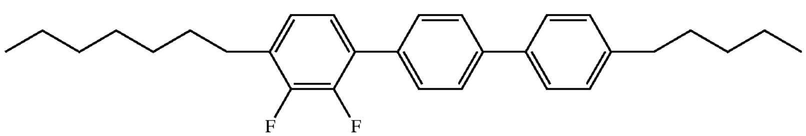 | X - 56 -> C - 106 -> A - 131 -> N - 136 -> I |
| 1674 | 5.00 | 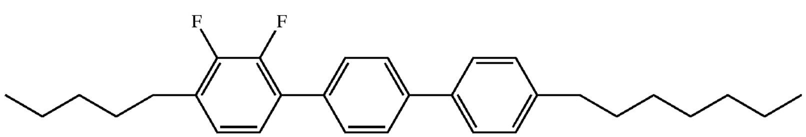 | X - 66 -> SI - 75 -> C - 119 -> A - 135 -> N - 137 -> I |
| 1701 | 8.00 | 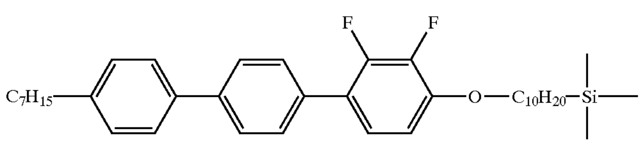 | |

TABLE 11-continued
MX number 9435
| Component | Percent | Structure | Phase diagram |
|---|---|---|---|
| 337 | 24.00 | 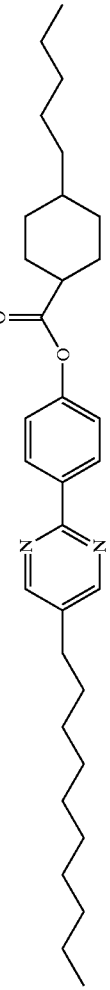 | I - 169 -> N - 105 -> C - 100 -> X; Q |
| 374 | 5.00 | 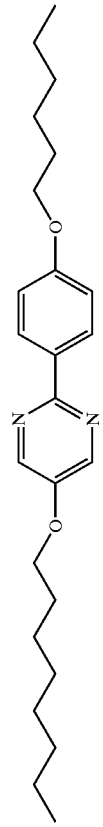 | |
| 5 | 9.00 | 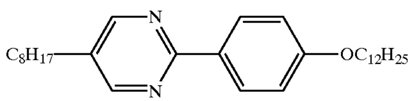 | X - 43.2 - C 62.4 A - 66.8 - N - 68.2 - I; |
| 913 | 4.00 | 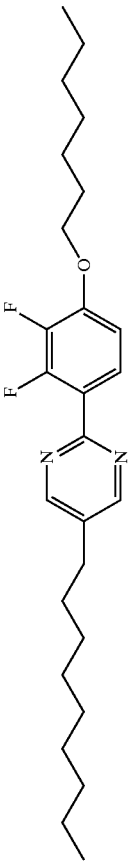 | I - 50 -> C - 32 -> X; X - 43 -> C - 50 -> I |
| 1598 | 4.00 | 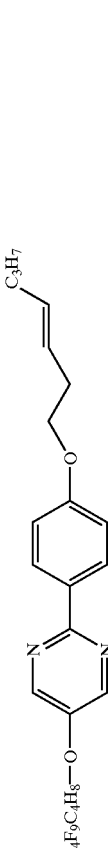 | |
| 1597 | 4.00 | 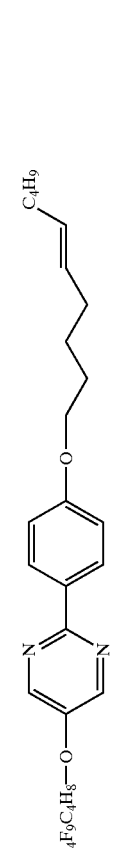 | |

TABLE 12

MX number 9441

| Component | Percent | Structure | Phase diagram |
|---|---|---|---|
| 950 | 4.00 | 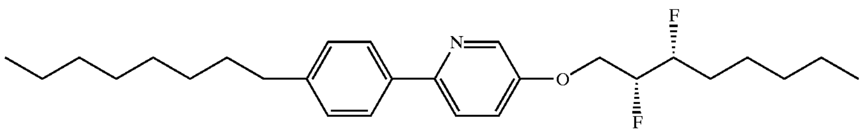 | I - 90 -> X; X - 94 -> I |
| 987 | 16.00 | 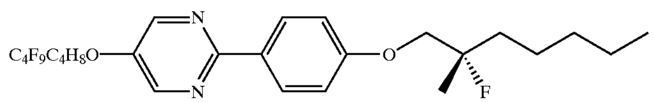 | I - 63 -> A - 54 -> C* - 21 -> X; X - 53 -> S? - 57 -> C* |
| 644 | 2.00 | 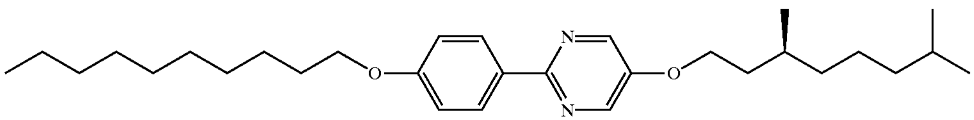 | I - 41 -> N - 20 -> X; X - 43 -> N - 47 -> I |
| 1673 | 10.00 | 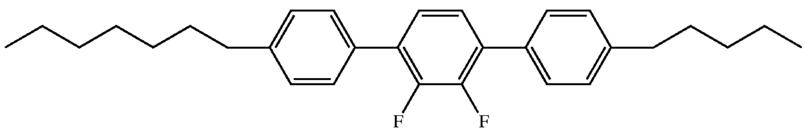 | X - 37 -> N - 112 -> I; C - 24 -> X |
| 1671 | 5.00 | 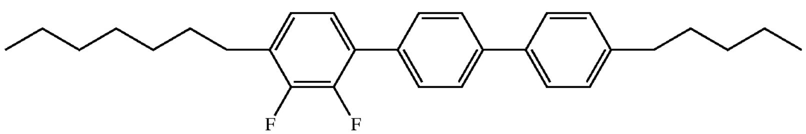 | X - 56 -> C - 106 -> A - 131 -> N - 136 -> I |
| 1674 | 5.00 | 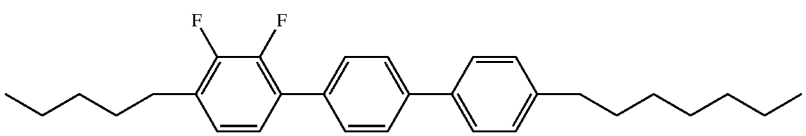 | X - 66 -> SI - 75 -> C - 119 -> A - 135 -> N - 137 -> I |
| 1701 | 10.00 | 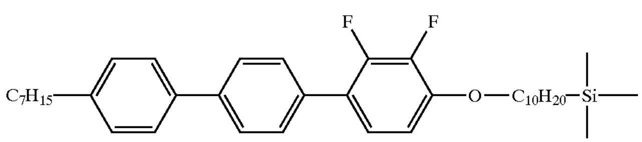 | |

TABLE 12-continued
MX number 9441
| Component | Percent | Structure | Phase diagram |
|---|---|---|---|
| 337 | 24.00 | 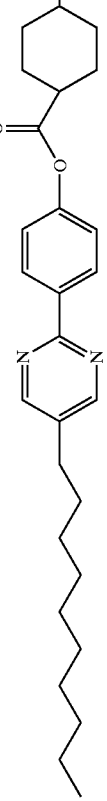 | I - 169 -> N - 105 -> C - 100 -> X; |
| 5 | 5.00 | 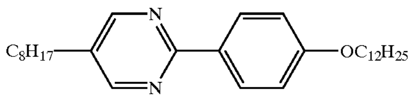 | X - 43.2 - C 62.4 A - 66.8 - N - 68.2 - I; |
| 913 | 7.00 | 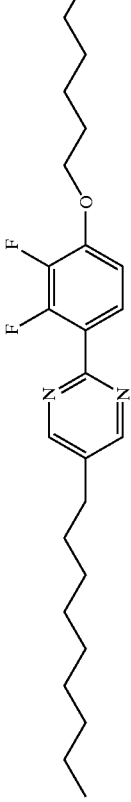 | |
| 1598 | 6.00 | 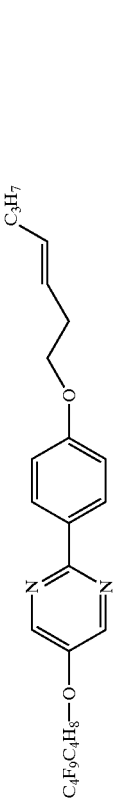 | I - 50 -> C - 32 -> X; X - 43 -> C - 50 -> I |
| 1597 | 6.00 | 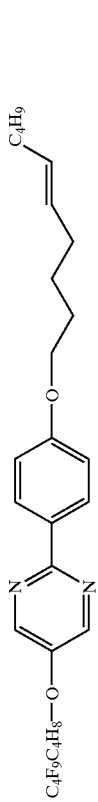 | |

TABLE 13
MX number 9451
| Component | Percent | Structure | Phase diagram |
|---|---|---|---|
| 003 | 18.13 | 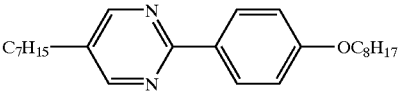 | X – 49 – A – 44 – N – 69.5 – I; |
| 004 | 19.45 | 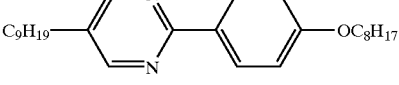 | X – 33 – C – 60 – A – 74.5 – I; |
| 005 | 19.45 | 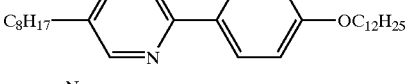 | X – 43.2 – C 62.4 A – 66.8 – N – 68.2 – I; |
| 987 | 19.68 | 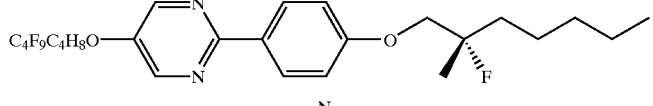 | I – 63 -> A – 54 -> C* – 21 -> X; X – 53 -> S? – 57 -> C* |
| 374 | 17.23 | 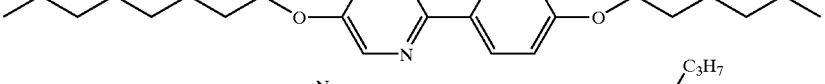 | |
| 1598 | 6.08 | 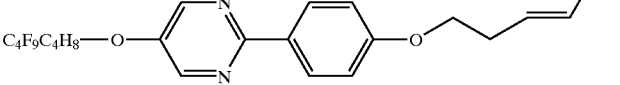 | |
TABLE 14
MX number 9452
| Component | Percent | Structure | Phase diagram |
|---|---|---|---|
| 003 | 18.10 | 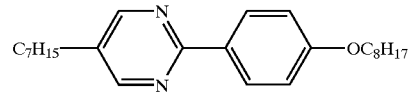 | X – 49 – A – 44 – N – 69.5 – I; |
| 004 | 19.42 | 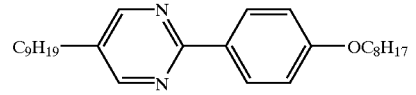 | X – 33 – C – 60 – A – 74.5 – I; |
| 005 | 19.42 | 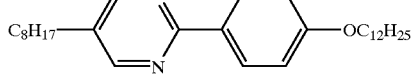 | X – 43.2 – C 62.4 A – 66.8 – N – 68.2 – I; |
| 987 | 18.21 | 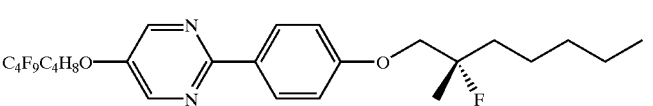 | I – 63 -> A – 54 -> C* – 21 -> X; X – 53 -> S? – 57 -> C* |
| 374 | 12.81 | 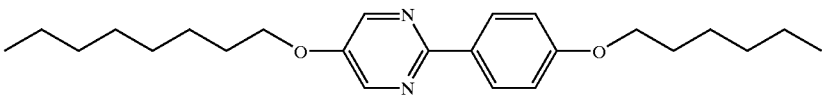 | |
| 1598 | 12.04 | 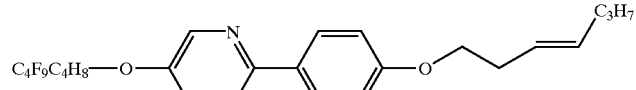 | |

TABLE 15
MX number 9454-001204
| Component | Percent | Structure | Phase diagram |
|---|---|---|---|
| 1139 | 7.50 | 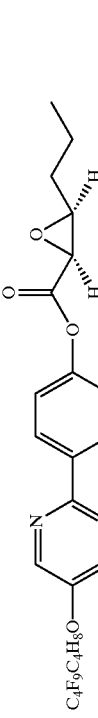 | I – 75 <– X; I <– 86 – X |
| 644 | 3.75 | 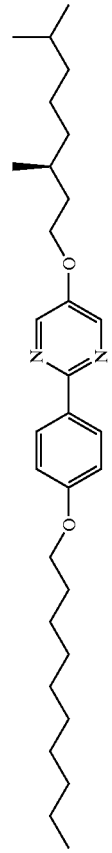 | I – 41 –> N – 20 –> X; X – 43 –> N – 47 –> I |
| 1598 | 12.50 | 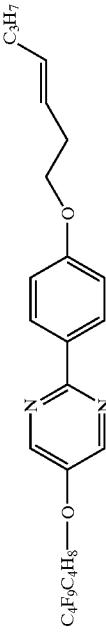 | |
| 1671 | 10.00 | 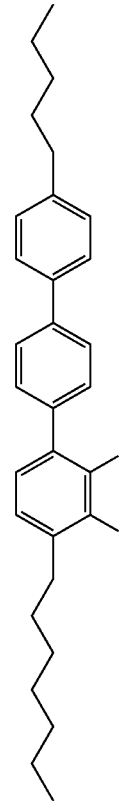 | X – 56 –> C – 106 –> A – 131 –> N – 136 –> I |
| 1674 | 10.00 | 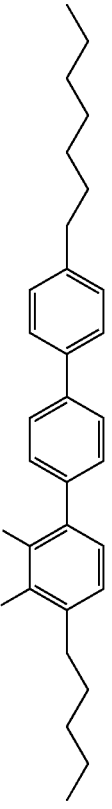 | X – 66 –> SI – 75 –> C – 119 –> A – 135 –> N – 137 –> I |

TABLE 15-continued

MX number 9454-001204

| Component | Percent | Structure | Phase diagram |
|---|---|---|---|
| 1673 | 17.50 | 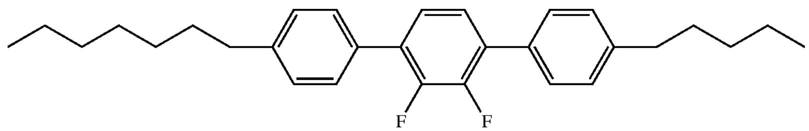 | X – 37 –> N – 112 –> I; C – 24 –> X |
| 337 | 31.25 | 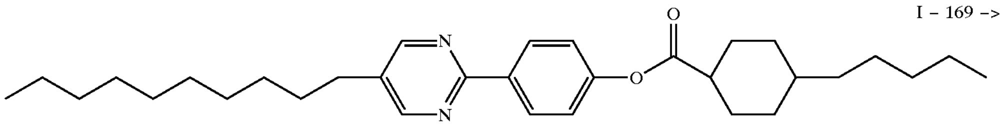 | I – 169 –> N – 105 –> C – 100 –> X |
| 374 | 3.75 | 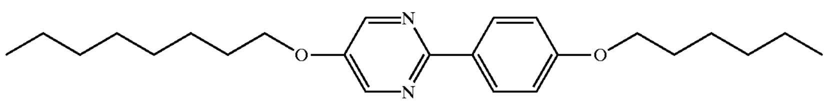 | |
| 5 | 3.75 | 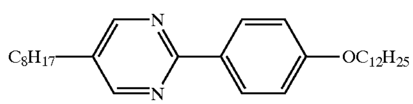 | X – 43.2 – C 62.4 A – 66.8 – N – 68.2 – I; |

TABLE 16
| MX # | Ps | Visc | E rise | Dielectric | Phase diagram | DSC MP | DSC FP |
|---|---|---|---|---|---|---|---|
| 9480 | 30.2 | 117.4 | 140 | 4.43 | I - 88 - N - 81.8 - A - 74.7 - C | −43 | <−60 |
| 8818 | 33.5 | 99.8 | 90 | 4.32 | I - 82.1 - N - 76 - A - 70.9 - C | −41.9 | −50.9 |
| 9486 | 31.8 | 158.6 | 110 | 4.58 | I - 82.9 - N - 80.9 - A - 74.2 - C | −42.7 | <−60 |
| 8818 | 33.5 | 89.8 | 90 | 4.32 | I - 82.1 - N - 76 - A - 70.9 - C | −41.9 | −50.9 |
TABLE 17
MX number 8818
| Component | Percent | Milligrams | Structure | Total percent 100 |
|---|---|---|---|---|
| 3 | 20.00 | |  C$_7$H$_{15}$— ... —OC$_8$H$_{17}$ | |
| | Converting to % | | | |
| 336 | 16.00 | | 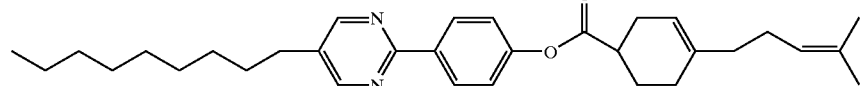 | |
| 576 | 13.00 | | 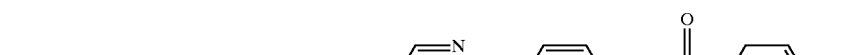 | |
| 644 | 2.00 | | 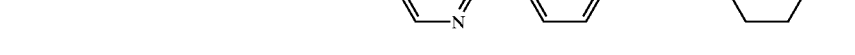 | |
| 913 | 9.00 | | 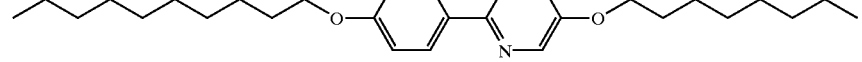 | |
| 942 | 13.00 | | 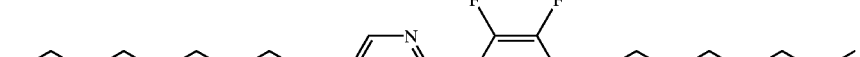 | |
| 950 | 4.00 | | 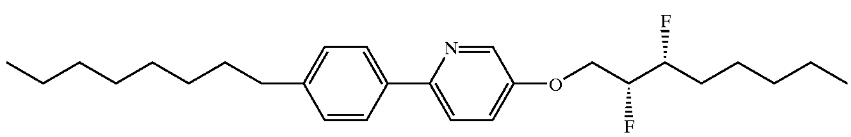 | |
| 987 | 18.00 | |  C$_4$F$_9$C$_4$H$_8$O— | |
| 1054 | 5.00 | | 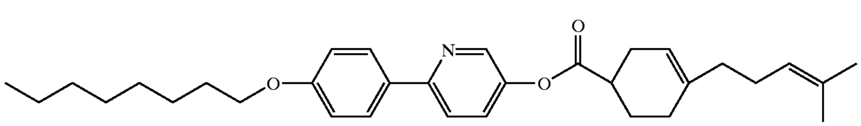 | |

What is claimed is:

1. A liquid crystal composition comprising one or more compounds of the formula:

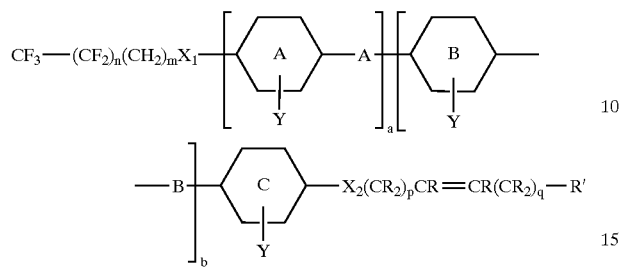

Formula I wherein:

a and b are 0 or 1;

A and B, independently, are selected from the group consisting of a single bond, —COO—, —OOC—, —CH$_2$—CH$_2$—, —OCH$_2$—, —CH$_2$—O—, —CH=CH— (cis or trans); —C≡C—, —CH=CH—CH=CH— (cis or trans);

Y represents up to four substituents on a given ring where the substituents are selected from a halogen, CN or NO$_2$;

Core rings A, B and C can be aromatic or alicyclic, if aromatic one or two ring carbons can be replaced with a heteroatom or if alicyclic rings can contain 3–10 carbon atoms and optionally can contain a double bond, wherein one or two CH$_2$ of the alicyclic ring can be replaced with O or a C=O group;

m and n are integers ranging from 1 to 20, inclusive; p is an integer ranging from 2 to 20, inclusive; q is 0 or an integer ranging from 1 to 20; inclusive; n+m is 4 to 20 and p+q is 4 to 20;

X$_1$ and X$_2$, independently, are —O— or a single bond; and

R and R', independent of other R or R' in the alkenyl tail are hydrogens or alkyl groups having from one to twenty carbon atoms.

2. The liquid crystal composition of claim 1 wherein the compound of formula I has a core selected from the cores listed below:

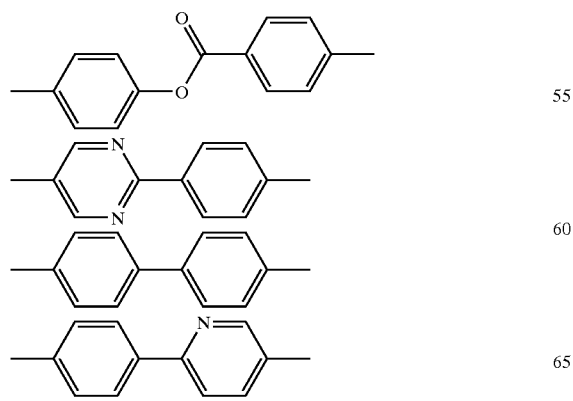

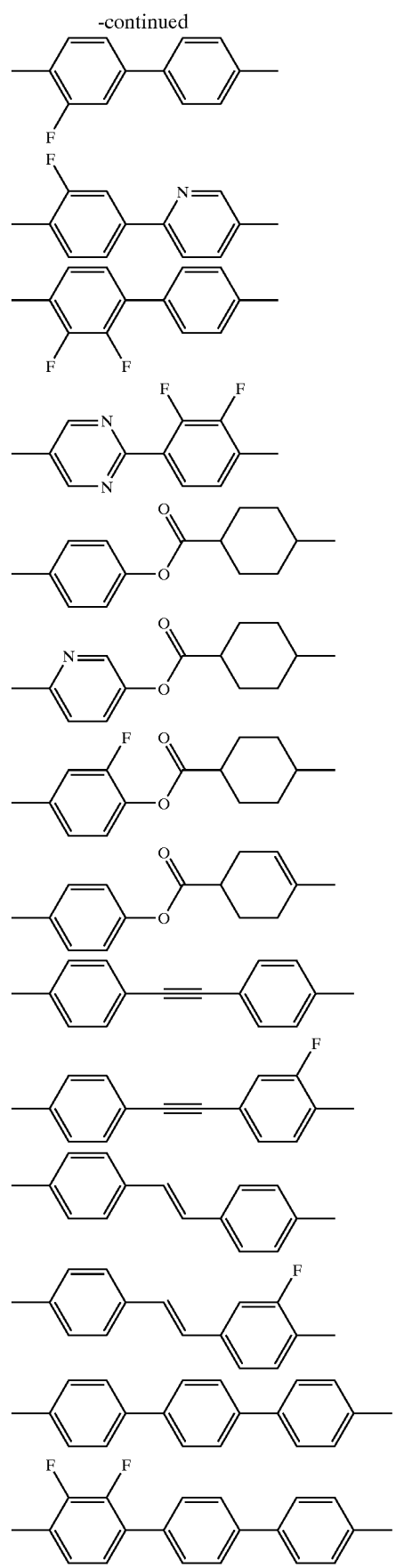

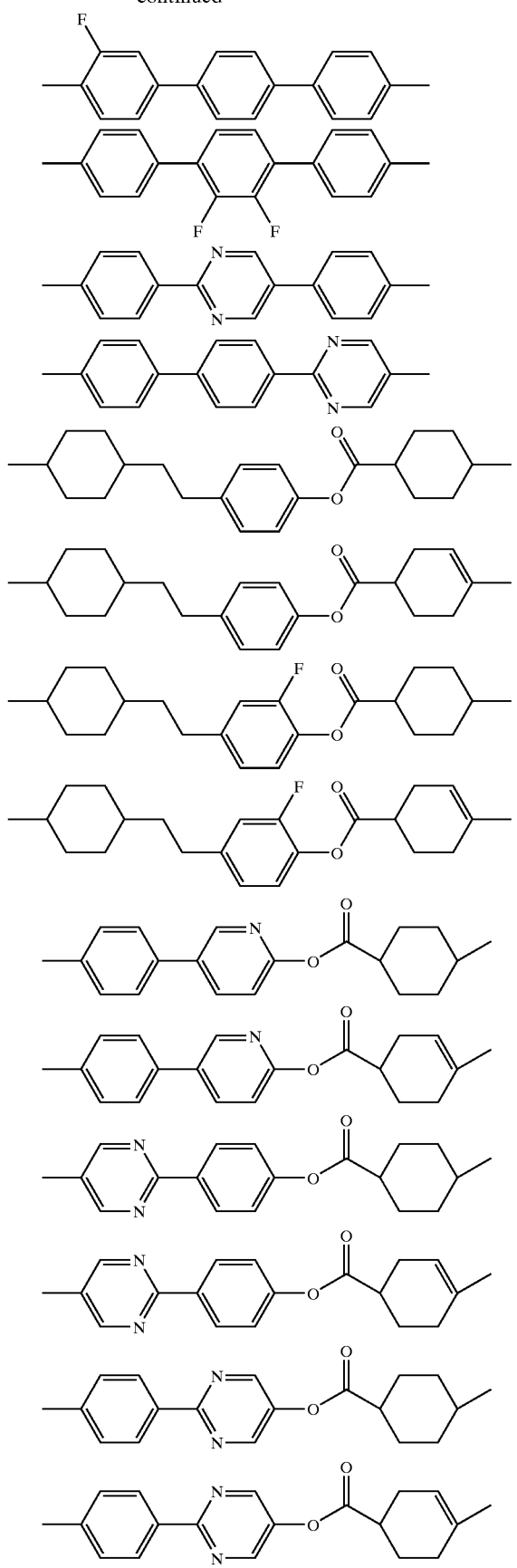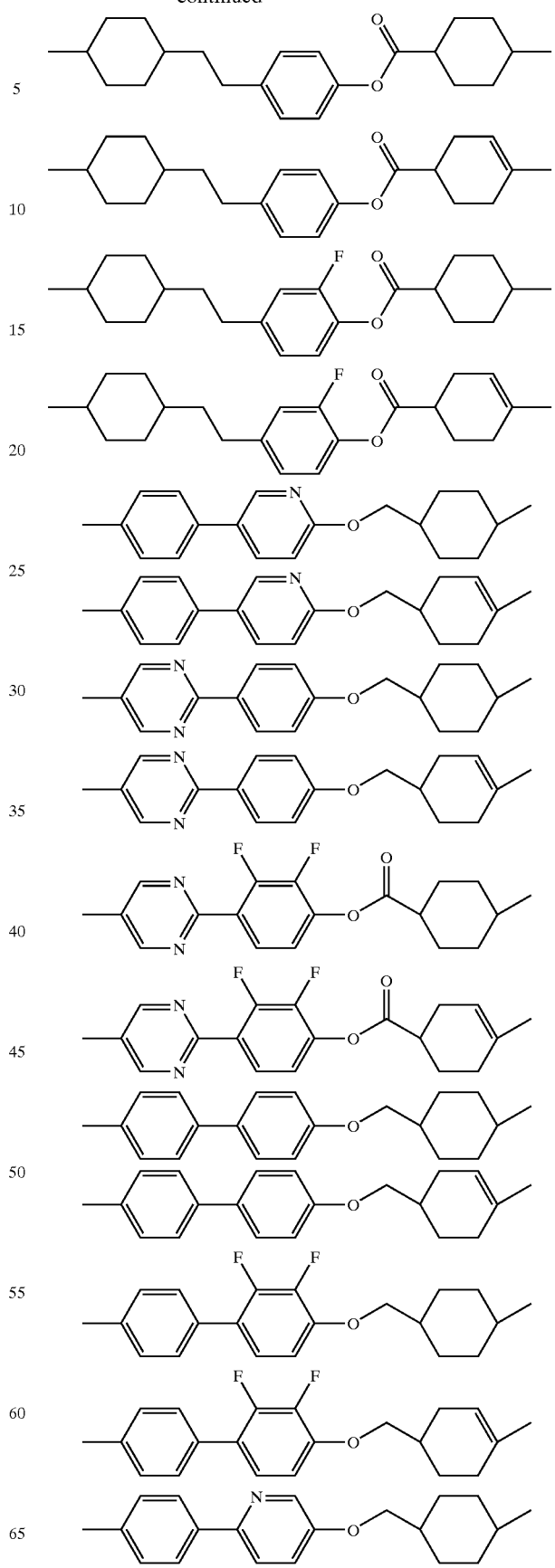

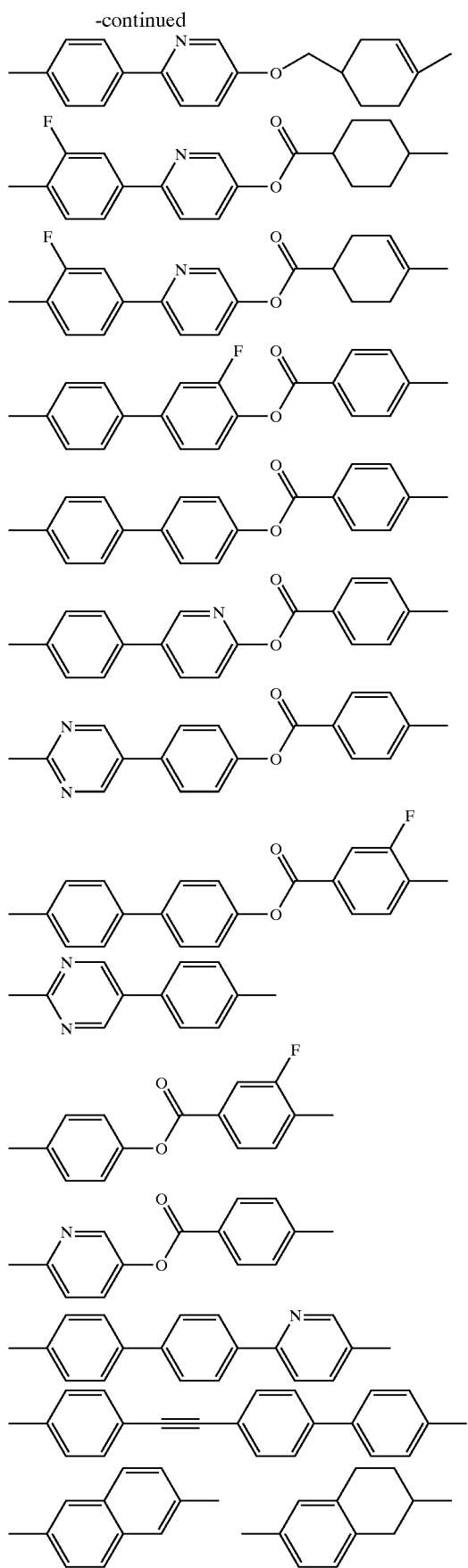
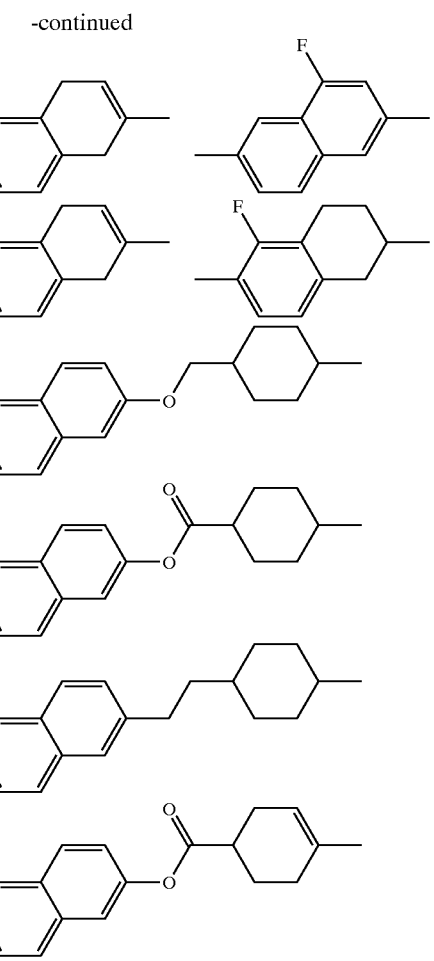

3. The liquid crystal composition of claim 1 wherein the compound of formula I has a phenyl pyrimidine core.

4. The liquid crystal composition of claim 1 that exhibits a smectic C phase.

5. The liquid crystal composition of claim 4 wherein the smectic C phase extends over a temperature range of 50° C. or more.

6. The liquid crystal composition of claim 4 that further exhibits a smectic A phase.

7. The liquid crystal composition of claim 1 which comprises two or more compounds of formula I.

8. The liquid crystal composition of claim 1 which comprises three or more compounds of formula I.

9. The liquid crystal composition of claim 1 further comprising one or more compounds of formula:

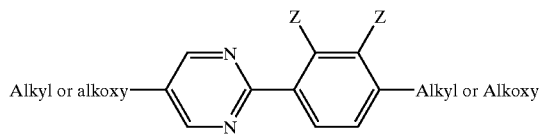

where Z can be CH or CF and the alkyl or alkoxy tails can be straight-chain or branched and contain from three to twenty carbon atoms.

10. The liquid crystal composition of claim 1 further comprising one or more compounds of formula:

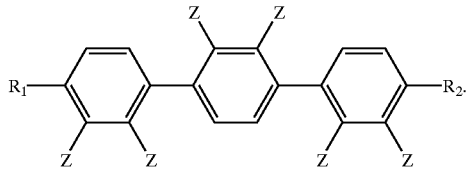

where Z is H or F and R1 and R2 are alkyl or alkoxy groups having from three to twenty carbon atoms.

11. The liquid crystal composition of claim 10 which comprises one compound of each of the formulas:

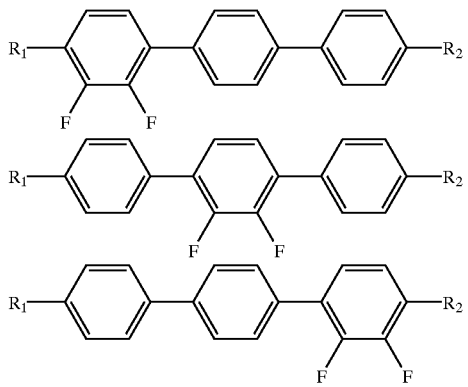

wherein $R_1$ and $R_2$ are alkyl or alkoxy groups having from three to twenty carbon atoms and $R_1$ is not the same as $R_2$.

12. The liquid crystal composition of claim 1 further comprising one or more compounds of formulas:

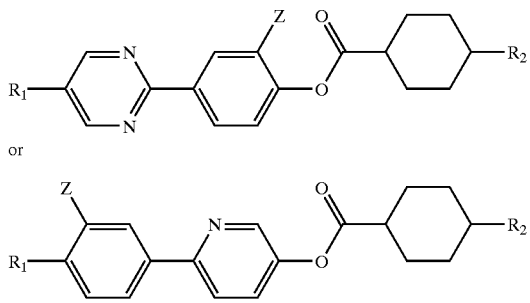

where Z is H or F and $R_1$ and $R_2$ are alkyl or alkoxy groups having three to twenty carbon atoms.

13. The liquid crystal composition of claim 9 further comprising one or more compounds of formulas:

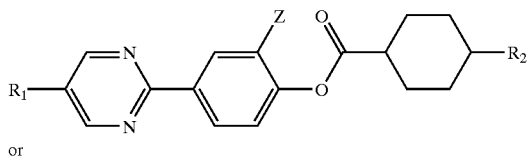

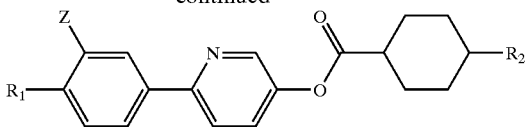

where Z is H or F and $R_1$ and $R_2$ are alkyl or alkoxy groups having three to twenty carbon atoms.

14. The liquid crystal composition of claim 9 further comprising one or more compounds of formula:

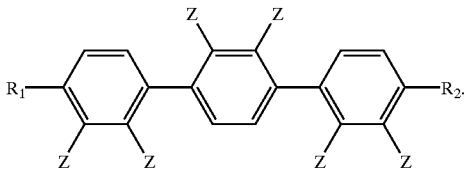

where Z is H or F and $R_1$ and $R_2$ are alkyl or alkoxy groups having from three to twenty carbon atoms.

15. The liquid crystal composition of claim 14 further comprising one or more compounds of formula:

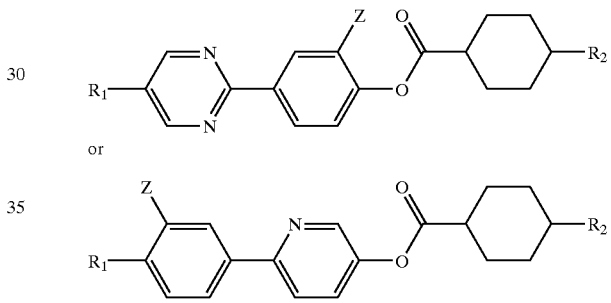

wherein Z is H or F and $R_1$ and $R_2$ are alkyl or alkoxy groups having from three to twenty carbon atoms.

16. The liquid crystal composition of claim 15 further comprising one or more compounds of formula:

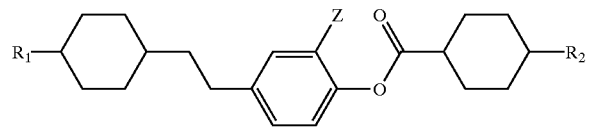

$R_1$ and $R_2$ are alkyl or alkoxy groups having from three to twenty carbon atoms Z is H or F.

17. The liquid crystal composition of claim 1 further comprising one or more compounds of formulas:

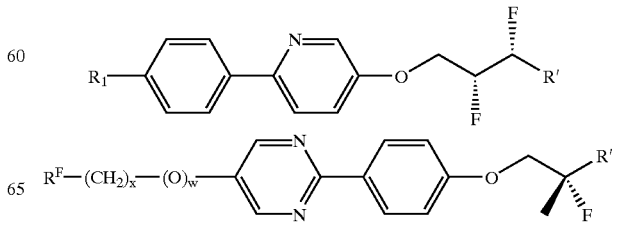

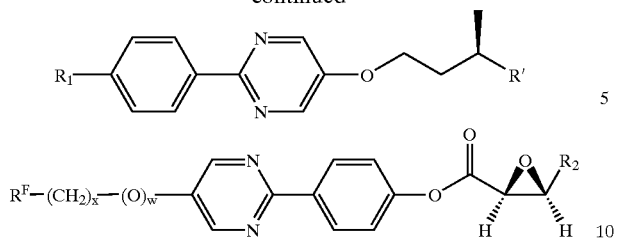

where: w is 0 or 1; x is an integer ranging from one to twenty; $R_1$ is an alkyl or alkoxy group having three to twenty carbon atoms; $R_2$ is an alkyl group having from three to twenty carbon atoms; R' is an alkyl group having three to twenty carbon atoms; and $R^F$ is a perfluoroalkyl group having from one to twenty carbon atoms.

18. The liquid crystal composition of claim 1 further comprising one or more compounds of formula:

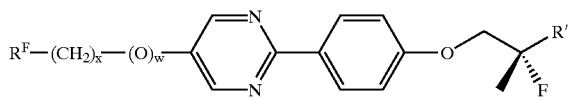

where: w is 0 or 1; x is an integer ranging from one to twenty; R' is an alkyl group having three to twenty carbon atoms; and $R^F$ is a perfluoroalkyl group having from one to twenty carbon atoms.

19. The liquid crystal composition of claim 1 further comprising one or more compounds of formula:

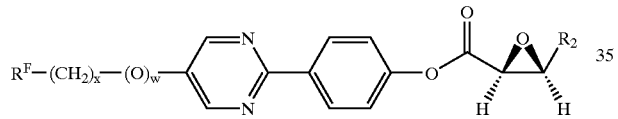

where: w is 0 or 1; x is an integer ranging from one to twenty; R2 is an alkyl group having from three to twenty carbon atoms; and $R^F$ is a perfluoroalkyl group having from one to twenty carbon atoms.

20. The liquid crystal composition of claim 1 which exhibits a freezing point of −60° C. or less.

21. The liquid crystal composition of claim 1 which exhibits both a smectic C and a smectic A phase.

22. The liquid crystal composition of claim 20 which further exhibits a freezing point of −60° C. or less.

23. A LC compound having the formula:

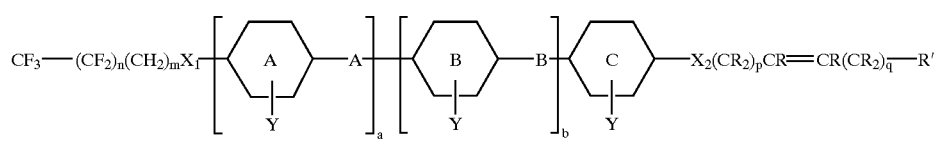

Formula I wherein:
  a and b are 0 or 1;
  A and B, independently, are selected from the group consisting of a single bond, —COO—, —OOC—, —CH₂—CH₂—, —OCH₂—, —CH₂—O—, —CH=CH— (cis or trans); —C≡C—, —CH=CH—CH=CH— (cis or trans);
  Y represents up to four substituents on a given ring where the substituents are selected from a halogen, CN or NO₂;
  Core rings A, B and C can be aromatic or alicyclic, if aromatic one or two ring carbons can be replaced with a heteroatom or if alicyclic rings can contain 3–10 carbon atoms and optionally can contain a double bond, wherein one or two CH₂ of the alicyclic ring can be replaced with O or a C=O group;
  m and n are integers ranging from 1 to 20, inclusive; p is an integer ranging from 2 to 20, inclusive; q is 0 or an integer ranging from 1 to 20; inclusive; n+m is 4 to 20 and p+q is 4 to 20;
  $X_1$ and $X_2$, independently, are —O— or a single bond; and
  R and R', independent of other R or R' in the alkenyl tail are hydrogens or alkyl groups having from one to twenty carbon atoms.

24. The liquid compound of claim 23 having a core selected from the cores listed below:

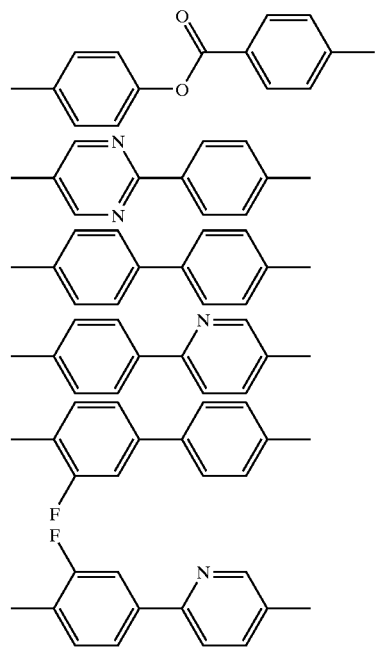

-continued

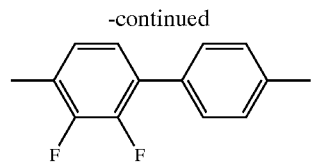

-continued
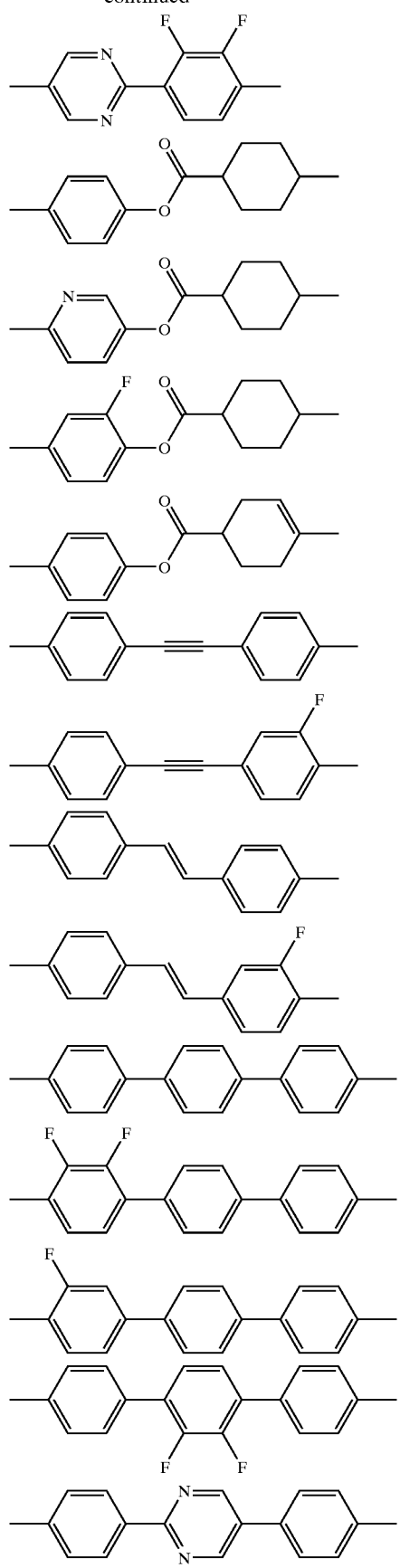
-continued
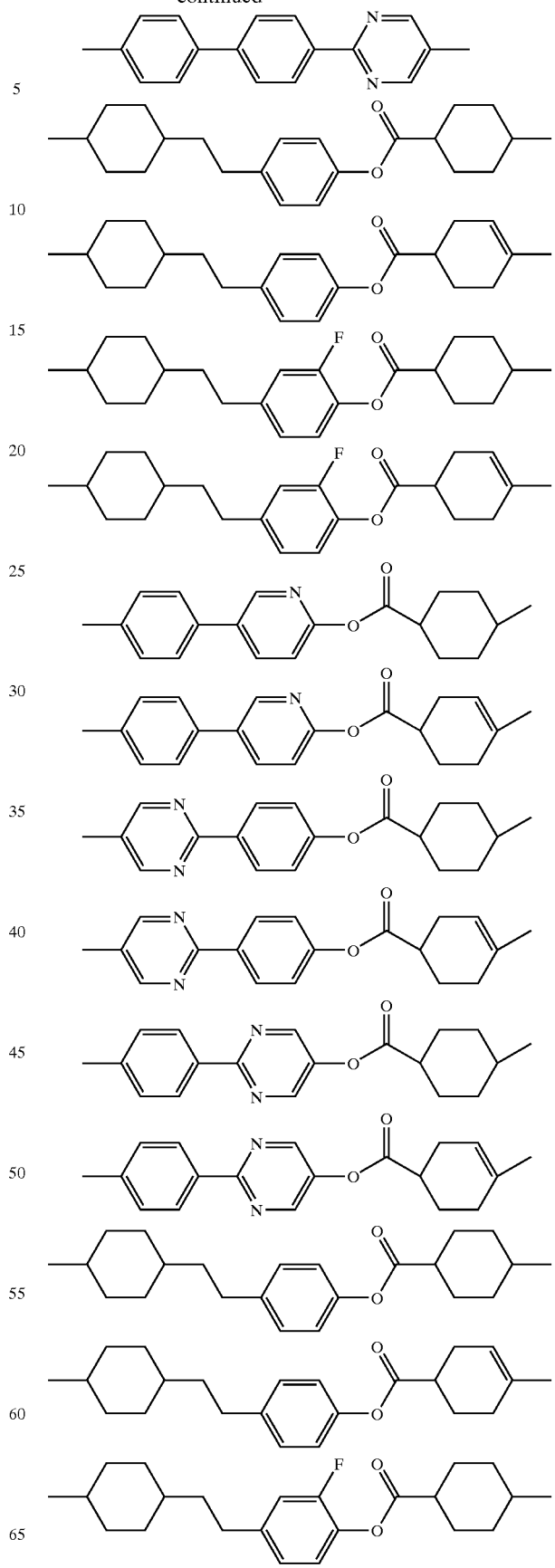

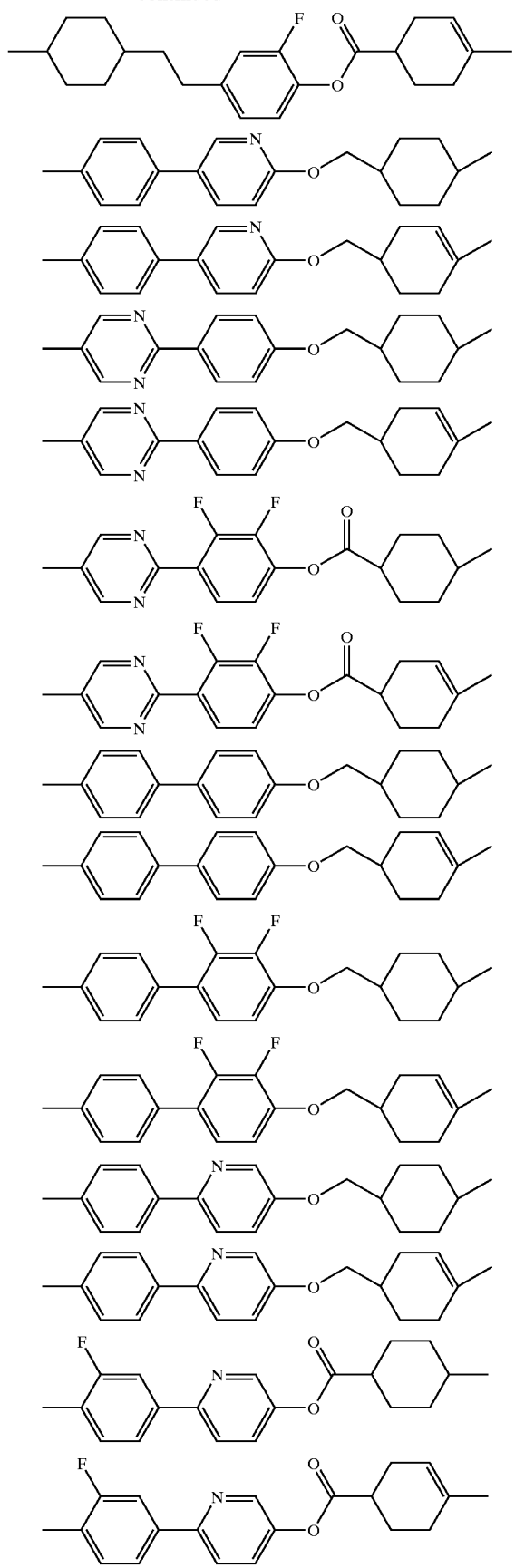
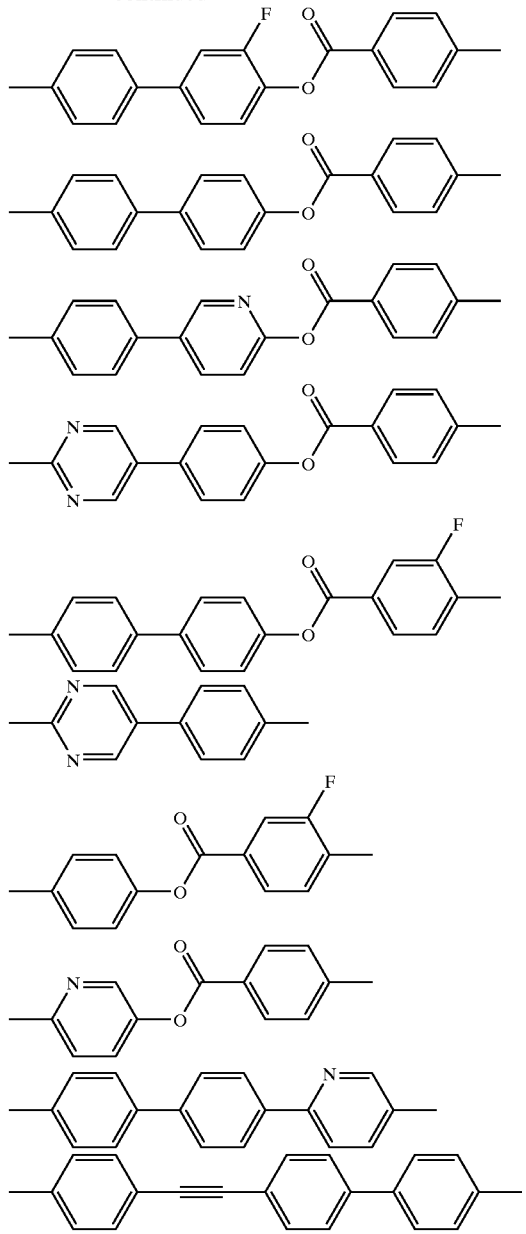

25. The liquid crystal compound of claim 23 which has a phenyl pyrimidine core.
26. The liquid crystal compound of claim 23 which has an optionally substituted terphenyl core.
27. The liquid crystal compound of claim 23 wherein $X_1$ is an oxygen.
28. The liquid crystal compound of claim 23 wherein $X_2$ is a single bond.
29. The liquid crystal compound of claim 23 wherein the double bond in the alkene tail is a cis double bond.
30. The liquid crystal compound of claim 23 wherein the double bond in the alkene tail is a trans double bond.
31. The liquid crystal compound of claim 23 wherein the core contains two aromatic rings.
32. The liquid crystal compound of claim 23 wherein the core contains a cyclohexane ring.
33. The liquid crystal compound of claim 23 wherein m+n ranges from 5 to 12.
34. The liquid crystal compound of claim 23 wherein n is 3 and m is 4.

35. The liquid crystal compound of claim 23 wherein the core is a phenylpyrimidine which is optionally substituted with one or two fluorines on the phenyl ring.

36. The liquid crystal compound of claim 35 wherein m+n ranges from 5 to 12.

37. The liquid crystal compound of claim 23 wherein m+n ranges from 8 to 12.

38. The liquid crystal compound of claim 36 wherein $X_1$ is an oxygen atom.

39. The liquid crystal compound of claim 36 wherein $X_2$ is a single bond.

40. The liquid crystal compound of claim 39 wherein p+q ranges from 5 to 12 and R' is a methyl group.

41. The liquid crystal compound of claim 39 wherein q is zero and R' is a hydrogen.

42. The liquid crystal compound of claim 39 wherein p is 3–6 inclusive and q is 3–6, inclusive, and R' is a hydrogen or a methyl group.

43. The liquid crystal compound of claim 39 wherein the double bond in the alkene tail is a cis double bond.

44. The liquid crystal compound of claim 39 wherein the double bond in the alkene tail is a trans double bond.

45. The liquid crystal compound of claim 23 wherein the alkene tail is a chiral nonracemic moiety.

46. The liquid crystal compound of claim 45 wherein in the alkene tail one R bonded to the third to the fifth carbon in the tail is a methyl group and the carbon to which the methyl group is bonded is an asymmetric carbon.

47. The liquid crystal compound of claim 46 wherein the alkene tail has the formula:

$$-O-(CH_2)r\text{-}C^*H(CH_3)-(CH_2)s\text{-}CH=C(CH_3)_2$$

where r is 2–6, inclusive and s is 2 to 6, inclusive.

48. The liquid crystal compound of claim 47 wherein r is 2 and s is 2 to 4, inclusive.

49. The liquid crystal compound of claim 48 wherein m+n ranges from 5 to 12, inclusive.

50. A liquid crystal device having an aligned layer of the LC composition of claim 1.

51. The device of claim 50 which is a surface-stabilized FLC device.

* * * * *

UNITED STATES PATENT AND TRADEMARK OFFICE
CERTIFICATE OF CORRECTION

PATENT NO.    : 6,759,101 B2
DATED         : July 6, 2004
INVENTOR(S)   : Gough et al.

It is certified that error appears in the above-identified patent and that said Letters Patent is hereby corrected as shown below:

Column 5,
Lines 33-35, delete "LC compositions of this invention include those that contain 3% or more of one or more of the compounds of this invention."

Column 9,
Lines 34 and 36, delete "propel" and replace with -- propyl --.

Column 11,
Line 18, delete "are" after "typically".

Column 16,
Line 15, after "Compound 4" insert -- (1598) --.

Columns 35 and 36,
Table 3, in the Percent column, delete two occurrences of "6 00" and replace with -- 6.00 --.

Column 41 and 42,
Table 4, in the Phase diagram column, fifth entry, delete "X - 48 ->C - 86 -> A - 90 -> 1;" and replace with -- X - 48 ->C - 86 -> A - 90 ->I; --

Column 43 and 44,
Table 4, in the Percent column, delete "4 00" and replace with -- 4.00 --, and delete "3 00" and replace with -- 3.00 --.

Columns 45 and 46,
Table 5, in the Percent column, last entry, delete "4 44" and replace with -- 4.44 --.

Columns 47 and 48,
Table 5, in the Percent column, fourth entry, delete "3 33" and replace with -- 3.33 --.

Columns 49 and 50,
Table 6, in the Percent column, first entry, delete "2 00" and replace with -- 2.00 --.

UNITED STATES PATENT AND TRADEMARK OFFICE
CERTIFICATE OF CORRECTION

PATENT NO. : 6,759,101 B2
DATED : July 6, 2004
INVENTOR(S) : Gough et al.

It is certified that error appears in the above-identified patent and that said Letters Patent is hereby corrected as shown below:

Column 88,
Line 65, delete "CH or CF" and replace with -- H or F --.

Signed and Sealed this

Seventeenth Day of May, 2005

JON W. DUDAS
*Director of the United States Patent and Trademark Office*